US008564315B2

(12) United States Patent
Fisseler et al.

(10) Patent No.: US 8,564,315 B2
(45) Date of Patent: Oct. 22, 2013

(54) DOWNHOLE CORROSION MONITORING

(75) Inventors: Patrick J. Fisseler, Missouri City, TX (US); Anthony R. H. Goodwin, Sugar Land, TX (US); Pierre Campanac, Sugar Land, TX (US); John W. Still, Katy, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 480 days.

(21) Appl. No.: 12/832,726

(22) Filed: Jul. 8, 2010

(65) Prior Publication Data

US 2012/0007617 A1   Jan. 12, 2012

(51) Int. Cl.
 *G01R 27/08* (2006.01)
(52) U.S. Cl.
 USPC ............... 324/700; 73/152.51; 166/250.01; 205/775
(58) Field of Classification Search
 USPC ........................................... 324/700
 See application file for complete search history.

(56) References Cited

U.S. PATENT DOCUMENTS

| | | | | |
|---|---|---|---|---|
| 4,863,572 A | * | 9/1989 | Jasinski | 205/775.5 |
| 4,902,981 A | * | 2/1990 | Gard et al. | 330/9 |
| 5,188,715 A | * | 2/1993 | Chen et al. | 205/776 |
| 5,627,749 A | * | 5/1997 | Waterman et al. | 702/6 |
| 5,858,204 A | * | 1/1999 | Jambo et al. | 205/775 |
| 6,253,847 B1 | * | 7/2001 | Stephenson | 166/248 |
| 6,641,434 B2 | | 11/2003 | Boyle et al. | |
| 6,939,717 B2 | * | 9/2005 | Jiang et al. | 436/121 |
| 6,986,282 B2 | * | 1/2006 | Ciglenec et al. | 73/152.51 |
| 7,061,255 B1 | * | 6/2006 | Foreman et al. | 324/700 |
| 7,114,562 B2 | | 10/2006 | Fisseler et al. | |
| 7,157,920 B2 | * | 1/2007 | Barber et al. | 324/700 |
| 7,239,156 B1 | * | 7/2007 | Hladky et al. | 324/700 |
| 7,245,132 B1 | * | 7/2007 | Poirier et al. | 324/700 |
| 7,265,559 B1 | * | 9/2007 | Hladky et al. | 324/700 |
| 7,368,050 B2 | | 5/2008 | Jovancicevic et al. | |
| 7,622,030 B2 | | 11/2009 | Gill et al. | |
| 7,686,938 B2 | | 3/2010 | Gill et al. | |
| 8,111,078 B1 | * | 2/2012 | Yang et al. | 324/700 |
| 2006/0109012 A1 | * | 5/2006 | Foreman et al. | 324/700 |
| 2006/0272809 A1 | * | 12/2006 | Tubel et al. | 166/250.01 |
| 2007/0229095 A1 | * | 10/2007 | Ramgopal et al. | 324/700 |
| 2008/0053212 A1 | * | 3/2008 | Brennan et al. | 73/152.26 |
| 2008/0169205 A1 | * | 7/2008 | Kim | 205/775.5 |
| 2008/0283418 A1 | | 11/2008 | Jovancicevic et al. | |
| 2009/0072832 A1 | * | 3/2009 | He et al. | 324/324 |
| 2009/0096471 A1 | * | 4/2009 | Eden | 324/700 |
| 2009/0188665 A1 | * | 7/2009 | Tubel et al. | 166/250.01 |
| 2009/0195260 A1 | * | 8/2009 | Bell et al. | 324/700 |
| 2010/0025110 A1 | * | 2/2010 | John et al. | 175/27 |
| 2011/0100641 A1 | * | 5/2011 | Briquet et al. | 166/373 |
| 2011/0272135 A1 | * | 11/2011 | Kaul et al. | 166/57 |
| 2012/0038377 A1 | * | 2/2012 | Hamann et al. | 324/700 |

\* cited by examiner

*Primary Examiner* — Melissa Koval
*Assistant Examiner* — Benjamin M Baldridge
(74) *Attorney, Agent, or Firm* — Cathy Hewitt; John Vereb

(57) ABSTRACT

Apparatus and methods for measuring an effect of corrosion with a corrosion sensor. The apparatus includes at least a portion of a metal material configured to be disposed within a borehole and exposed to a fluid. The apparatus includes a sensor configured to measure an effect of corrosion of the at least portion of the metal material within the fluid.

16 Claims, 10 Drawing Sheets

DOWNHOLE CORROSION MONITORING

BACKGROUND OF THE DISCLOSURE

Wells are generally drilled into the ground or ocean bed to recover natural deposits of oil and gas, as well as other desirable materials that are trapped in geological formations in the Earth's crust. Wells are typically drilled using a drill bit attached to the lower end of a "drill string." Drilling fluid, or mud, is typically pumped down through the drill string to the drill bit. The drilling fluid lubricates and cools the bit, and may additionally carry drill cuttings from the borehole back to the surface.

In various oil and gas exploration operations, it may be beneficial to have information about the fluids contained in the subterranean formations that are penetrated by a borehole. For example, certain formation evaluation schemes include measurement and analysis of the fluids extracted from the subterranean formations. These measurements may be essential to designing the production facility and predicting the lifetime thereof.

Reservoir well creation and/or testing may involve drilling into the subterranean formation and the monitoring of various subterranean formation parameters. As such, downhole tools may be exposed to increasingly hostile environments, such as by having increased downhole pressure, temperature, increased level of shock and vibration, in addition to increasingly corrosive environments. For example, as the corrosivity of downhole environments increases, the useful life of the downhole tools in these environments may be reduced, such as by limiting the useful life of the downhole tools to only 100 to 200 hours while downhole. In addition, as the corrosivity of subterranean formation fluids increases, these formation fluids may influence the choice of materials to be used in production facilities and/or reduce the useful life of such production facilities.

Corrosivity is normally increased in high sulfide and/or carbon dioxide environments, as well as in aqueous environments having a large concentration of sodium chloride, such as those environments present in the Middle East.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figures 1A, 1B:
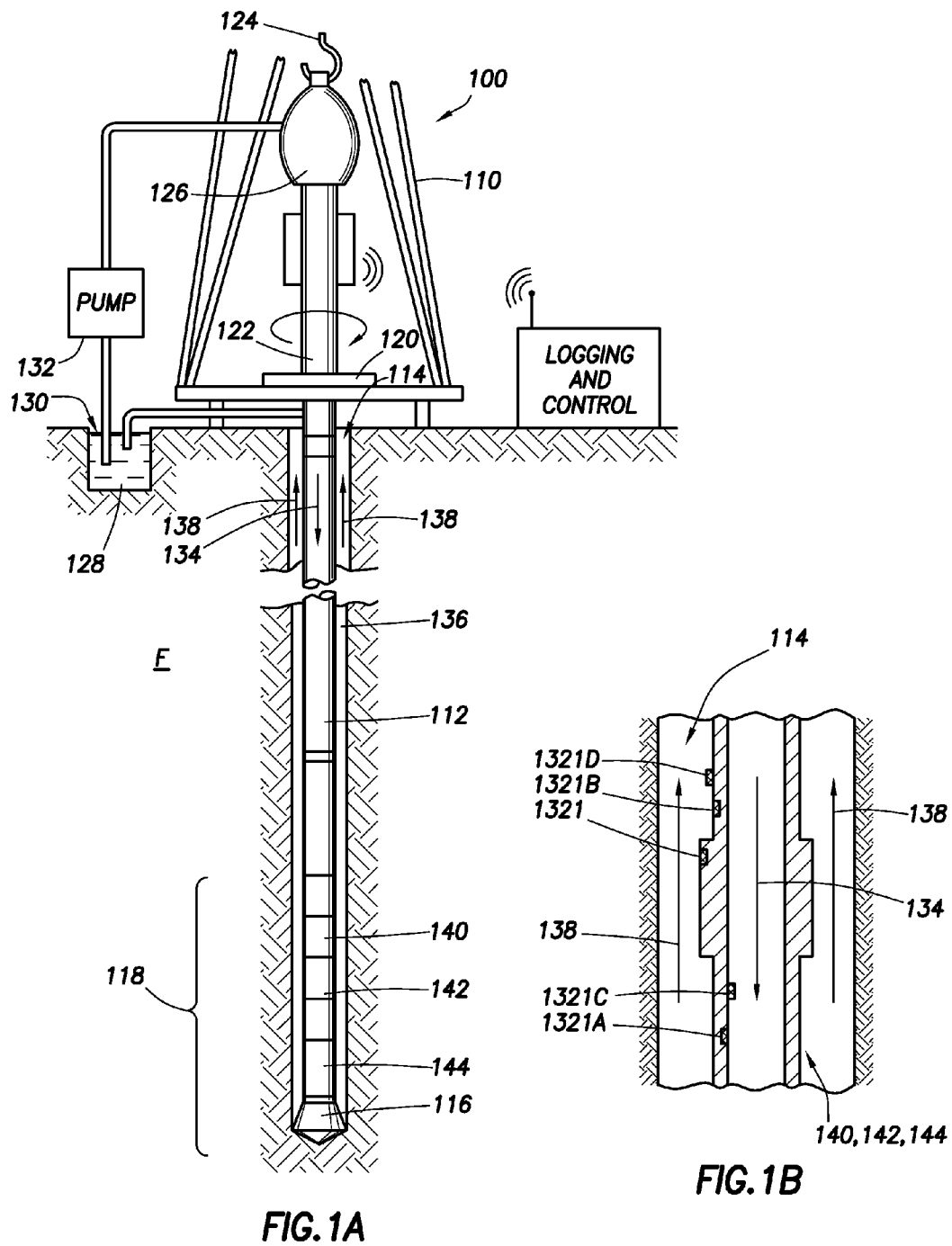
FIGS. 1A and 1B are schematic views of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the subterranean formation of a first feature over or on a second feature in the description that follows may include embodiments in which the first and second features are formed in direct contact, and may also include embodiments in which additional features may be formed interposing the first and second features, such that the first and second features may not be in direct contact.

In accordance with the present disclosure, a corrosion sensor, and according to one or more methods of use thereof, may be included within one or more of downhole tools and/or other components and devices that may be disposed within a borehole traversing subterranean formation. A metal material, for example the material in use in the downhole tool, may be disposed within a borehole of a subterranean formation, in which the corrosion sensor may be used to measure an effect of corrosion of the metal material, or at least a portion thereof. The metal material may be exposed to a fluid, such as by having the metal material in direct contact with the fluid, in which the fluid may be a drilling fluid, a completion fluid, an injection fluid, and/or a subterranean formation fluid. As the corrosion effect is measured, this measurement may be transmitted from a downhole tool to a surface unit, such as by using a telemetry unit coupled to the corrosion sensor.

The measured effect of corrosion may then be received at the surface unit, in which this measured corrosion effect may be analyzed or examined to determine if the corrosion effect is acceptable or unacceptable, such as if the fluid contacting the metal material is too corrosive for the current downhole application. For example, when the measured corrosion effect is received at the surface unit, this measured corrosion effect may be compared with corrosion effects of the metal material measured in laboratory and deemed acceptable. The measured corrosion effect may be compared with a predetermined range of values associated with the metal material. The predetermined range may be based upon acceptable values of the corrosion effect of the metal material when used at pressure and temperature conditions similar to those of the intended downhole application. Based on the analysis or the examination of the measured effect of corrosion, corrective actions may be performed, damage of metal material caused by corrosion may be monitored, completion alloys may be selected, and/or influx of gas from formation into the borehole may be estimated, among other uses of the measured effect of corrosion.

For example, an acceptable range of the effect of corrosion may enable the downhole tool to effectively and efficiently operate in contact with a drilling fluid for a sufficient duration within the downhole environment (e.g., within the drilling fluid at the downhole temperature and pressure conditions). If, for example, the measured corrosion effect is outside of the acceptable range and/or the measured corrosion effect is larger than an acceptable value, then the measured corrosion effect may indicate that the corrosion is too fast or too intense for the downhole tool to operate effectively and efficiently for a sufficient duration. In downhole environment, the drilling fluid may then corrode the downhole tool at an undesired rate, thereby excessively reducing the useful life of the downhole tool. Accordingly, the measured effect of corrosion may be analyzed or examined by a user and/or by a control system disposed at the surface. For example, the control system may alert a user, such as providing the user with a warning, if the control system determines that the value of the measured corrosion effect is unacceptable and/or that the drilling fluid is too corrosive for the downhole tool in the current downhole application. Based upon the measured corrosion effect, the composition of the drilling fluid in the borehole may be modified, such as by adding one or more components to the drilling fluid, thereby adjusting the corrosion speed or intensity. Alternatively, the downhole tool may be retrieved from the borehole before a catastrophic failure occurs, and the downhole tool may be replaced by another downhole tool more resistant to corrosion. The other downhole tool may further be selected based on the analysis or examination of the measured corrosion effect.

The corrosion sensor may be configured to measure an effect of corrosion of any metal material, including, but not limited to, metallic alloy portions of downhole tool housings, wireline cables, and/or specimen of completion alloys. The corrosion sensor may be configured to measure an effect of corrosion by any fluid to which downhole tools and/or completion equipments may be exposed. For example, the fluid may be drilling fluid that is pumped from the surface and through a passage formed within the downhole tool, the fluid may be drilling fluid that is flowing back upwardly between the downhole tool and the borehole, and/or the fluid may be fluid emitted into the borehole from subterranean formations and/or extracted from the subterranean formation into the downhole tool. As such, the downhole tool may include one or more corrosion sensors coupled thereto, in which the corrosion sensors may be disposed at one or more locations with respect to the downhole tool to measure an effect of corrosion by one or more fluids at the one or more locations.

Referring now to FIG. 1A, a schematic view of a wellsite 100 having a drilling rig 110 with a drill string 112 suspended therefrom is shown. The wellsite 100 shown, or one similar thereto, may be used at onshore and/or offshore locations. A borehole 114 may be formed into a subterranean formation F, such as by using rotary drilling, or any other method future-developed or known in the art. As such, the present disclosure may be used within a wellsite similar to the one shown in FIG. 1A. Those having ordinary skill in the art will appreciate however that the present disclosure may be used within other wellsites or drilling operations, such as within a directional drilling operations, without departing from the scope of the present disclosure.

Continuing with FIG. 1A, the drill string 112 may suspend from the drilling rig 110 into the borehole 114. The drill string 112 may include a bottom hole assembly ("BHA") 118 and a drill bit 116, in which the drill bit 116 may be disposed at an end of the drill string 112. The wellsite 100 may have the drilling rig 110 positioned over the borehole 114, and the drilling rig 110 may include a rotary table 120, a kelly 122, a traveling block or hook 124, and may additionally include a rotary swivel 126. The rotary swivel 126 may be suspended from the drilling rig 110 through the hook 124, and the kelly 122 may be connected to the rotary swivel 126 such that the kelly 122 may rotate with respect to the rotary swivel.

An upper end of the drill string 112 may be connected to the kelly 122, such as by threadingly connecting the drill string 112 to the kelly 122, and the rotary table 120 may rotate the kelly 122, thereby rotating the drill string 112 connected thereto. As such, the drill string 112 may be able to rotate with respect to the hook 124. Those having ordinary skill in the art, however, will appreciate that though a rotary drilling system is shown in FIG. 1A, other drilling systems may be used without departing from the scope of the present disclosure. For example, a top-drive (also known as a "power swivel") system may be used in accordance with the present disclosure. In such a top-drive system, the hook 124, swivel 126, and kelly 122 are replaced by a drive motor (electric or hydraulic) that may apply rotary torque and axial load directly to drill string 112.

The wellsite 100 may include drilling fluid 128 (also known as drilling "mud") stored in a pit 130. The pit 130 may be formed adjacent to the wellsite 100, as shown, in which a pump 132 may be used to pump the drilling fluid 128 into the borehole 114. The pump 132 may pump and deliver the drilling fluid 128 into and through a port of the rotary swivel 126, thereby enabling the drilling fluid 128 to flow into and downwardly through the drill string 112, the downward flow of the drilling fluid 128 being indicated generally by direction arrow 134. This drilling fluid 128 may then exit the drill string 112 through one or more ports disposed within and/or fluidly connected to the drill string 112. For example, the drilling fluid 128 may exit the drill string 112 through one or more ports formed within the drill bit 116.

As such, the drilling fluid 128 may flow back upwardly through the borehole 114, such as through an annulus 136 formed between the exterior of the drill string 112 and the interior of the borehole 114, the upward flow of the drilling fluid 128 being indicated generally by direction arrow 138. With the drilling fluid 128 following the flow pattern of direction arrows 134 and 138, the drilling fluid 128 may be able to lubricate the drill string 112 and the drill bit 116, and/or may be able to carry formation cuttings formed by the drill bit 116 (or formed by any other drilling components disposed within the borehole 114) back to the surface of the wellsite 100. This drilling fluid 128 may be filtered and cleaned and/or returned back to the pit 130 for recirculation within the borehole 114.

Though not shown, the drill string 112 may include one or more stabilizing collars. A stabilizing collar may be disposed within and/or connected to the drill string 112, in which the stabilizing collar may be used to engage and apply a force against the wall of the borehole 114. This may enable the stabilizing collar to prevent the drill string 112 from deviating from the desired direction for the borehole 114. For example, during drilling, the drill string 112 may "wobble" within the borehole 114, thereby allowing the drill string 112 to deviate from the desired direction of the borehole 114. This wobble action may also be detrimental to the drill string 112, components disposed therein, and the drill bit 116 connected thereto. However, a stabilizing collar may be used to minimize, if not overcome altogether, the wobble action of the drill string 112, thereby possibly increasing the efficiency of the drilling performed at the wellsite 100 and/or increasing the overall life of the components at the wellsite 100.

As discussed above, the drill string 112 may include a bottom hole assembly 118, such as by having the bottom hole assembly 118 disposed adjacent to the drill bit 116 within the drill string 112. The bottom hole assembly 118 may include one or more components included therein, such as components to measure, process, and store information. The bottom hole assembly 118 may include components to communicate and relay information to the surface of the wellsite.

As such, in FIG. 1A, the bottom hole assembly 118 may include one or more logging-while-drilling ("LWD") tools 140 and/or one or more measuring-while-drilling ("MWD") tools 142. The bottom hole assembly 118 may also include a steering-while-drilling system (e.g., a rotary-steerable system) and motor 144, in which the rotary-steerable system and motor 144 may be coupled to the drill bit 116.

The LWD tool 140 shown in FIG. 1A may include a thick-walled housing, commonly referred to as a drill collar, and may include one or more of a number of logging devices known in the art. Thus, the LWD tool 140 may be capable of measuring, processing, and/or storing information therein, as well as communicating with equipment disposed at the surface of the wellsite 100.

The MWD tool 142 may also include a housing (e.g., drill collar), and may include one or more of a number of measuring tools known in the art, such as tools used to measure characteristics of the drill string 112 and/or the drill bit 116. The MWD tool 142 may also include an apparatus for generating and distributing power within the bottom hole assembly 118. For example, a mud turbine generator powered by flowing drilling fluid therethrough may be disposed within the MWD tool 142. Alternatively, other power generating sources and/or power storing sources (e.g., a battery) may be disposed within the MWD tool 142 to provide power within the bottom hole assembly 118. As such, the MWD tool 142 may include one or more of the following measuring tools: a weight-on-bit measuring device, a torque measuring device, a vibration measuring device, a shock measuring device, a stick slip measuring device, a direction measuring device, an inclination measuring device, and/or any other device known in the art used within an MWD tool. It is contemplated to incorporate one or more of the tools and/or other devices shown in FIG. 1A with one or more aspects of the present disclosure.

Accordingly, the present disclosure contemplates coupling one or more corrosion sensors to a drilling tool and/or a drilling string, such as shown in FIG. 1A. For example, in FIG. 1B, a downhole drilling tool 140, 142, and/or 144, or a component thereof, may include one or more corrosion sensors 1321, in which the corrosion sensors 1321 may be coupled to one or more locations on the tool. The corrosion sensors 1321 may be provided on the downhole drilling tools 140, 142, and/or 144, such as in contact with the flow of drilling fluid 134 in an interior or inner bore of the downhole drilling tools 140, 142, and/or 144, as shown with corrosion sensors 1321A and 1321C. The corrosion sensors 1321 may also be provided on the downhole drilling tool 140, 142, and/or 144, such as in contact with the flow of drilling fluid 138 in the borehole annulus or in exterior of the downhole drilling tool 140, 142, and/or 144, as shown with corrosion sensors 1321B and 1321D. The corrosion sensors 1321 may be recessed within an outer surface of the downhole drilling tools 140, 142, and/or 144, such as shown with corrosion sensors 1321A and 1321B. The corrosion sensors 1321 may alternatively be protruding from a contact surface between the tool 140, 142, and/or 144 and the drilling fluid, such as shown with corrosion sensors 1321C and 1321D. Additionally, one or more corrosion sensors may be included up hole, such as on the surface of the drilling rig 110 shown in FIG. 1A. For example, one or more corrosion sensors may be included within and/or in fluid communication with the pipes carrying drilling fluid 128 towards and/or from the mud pit 130. This arrangement may enable monitoring of fluids going into the borehole 114, fluids within the borehole 114, and fluids coming out of the borehole 114 to measure the effect of corrosion on metallic materials present in the downhole drilling tools 140, 142, and/or 144, among other components of the drill string 112.

In operation, as a subterranean formation is drilled, such as to form a borehole, the drilling fluid within the borehole may change because of the influx of gas and/or fluid from the subterranean formation. This may affect the drilling fluid properties in a negative manner, such as by resulting in corrosion of portions of drilling tools, such as collars and/or electronic housings, by the drilling fluid and/or the mixture of drilling fluid and fluid from the subterranean formation. According to one or more aspects of the present disclosure, detecting and/or determining the effect of corrosion of the drilling tools by the drilling fluid may be performed in situ, that is, at downhole temperature and pressure conditions. If the corrosion by the drilling fluid is monitored downhole, particularly in real time, a field engineer, for example, may be alerted when the effects of corrosion of the drilling tools are within a predetermined range. This may enable the field engineer to take the appropriate action in a timely manner, for example to prevent damage to the downhole tools. Thus, the field engineer may decide to retrieve the drilling tools from the borehole before a catastrophic failure occurs. The field engineer may change the composition of the drilling mud being pumped into the borehole.

In addition, the corrosion by the drilling fluid that is monitored downhole may be used to estimate the damage of the drilling tools, for example by combining the strength or speed of the corrosion as indicated by the downhole corrosion sensors and the duration of the exposure of the drilling tool to the corrosion having this strength. The estimated damage may be used to plan or schedule inspection of the downhole drilling tools.

Figure 2A:
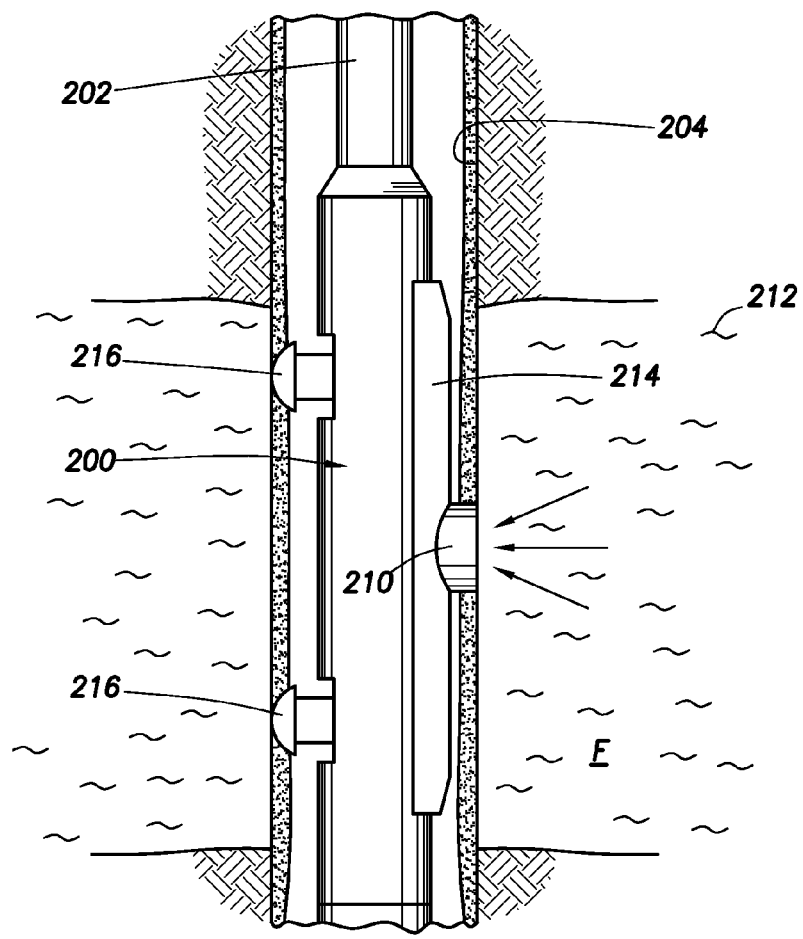
FIGS. 2A and 2B are schematic views of apparatus according to one or more aspects of the present disclosure.

Referring now to FIG. 2A, a schematic view of a tool 200 in accordance with one or more aspects of the present disclosure is shown. The tool 200 may be connected to and/or included within a drill string 202, in which the tool 200 may be disposed within a borehole 204 formed within a subterranean formation F. The tool 200 may be included and used within a bottom hole assembly, as described above.

The tool 200 may include a sampling-while drilling ("SWD") tool, such as that described in U.S. Pat. No. 7,114,562, filed on Nov. 24, 2003, entitled "Apparatus and Method for Acquiring Information While Drilling," and incorporated herein by reference in its entirety. The tool 200 may include a probe 210 to hydraulically establish communication with the subterranean formation F and draw formation fluid 212 into the tool 200.

The tool 200 may also include a stabilizer blade 214 and/or one or more pistons 216. The probe 210 may be disposed on the stabilizer blade 214 and extend therefrom to engage the wall of the borehole 204. The pistons, if present, may also extend from the tool 200 to assist probe 210 in engaging with the wall of the borehole 204. Alternatively, though, the probe 210 may not necessarily engage the wall of the borehole 204 when drawing fluid.

Fluid 212 drawn into the tool 200 may be measured to determine one or more parameters of the subterranean formation F, such as pressure and/or pretest parameters of the subterranean formation F. Additionally, the tool 200 may include one or more devices, such as sample chambers or sample bottles, which may be used to collect formation fluid samples. These formation fluid samples may be retrieved back at the surface with the tool 200. Alternatively, rather than collecting formation fluid samples, the formation fluid 212 received within the tool 200 may be circulated back out into the subterranean formation F and/or borehole 204. A pumping system may be included within the tool 200 to pump the formation fluid 212 circulating within the tool 200. For example, the pumping system may be used to pump formation fluid 212 from the probe 210 to the sample bottles and/or back into the subterranean formation F.

Figure 2B:
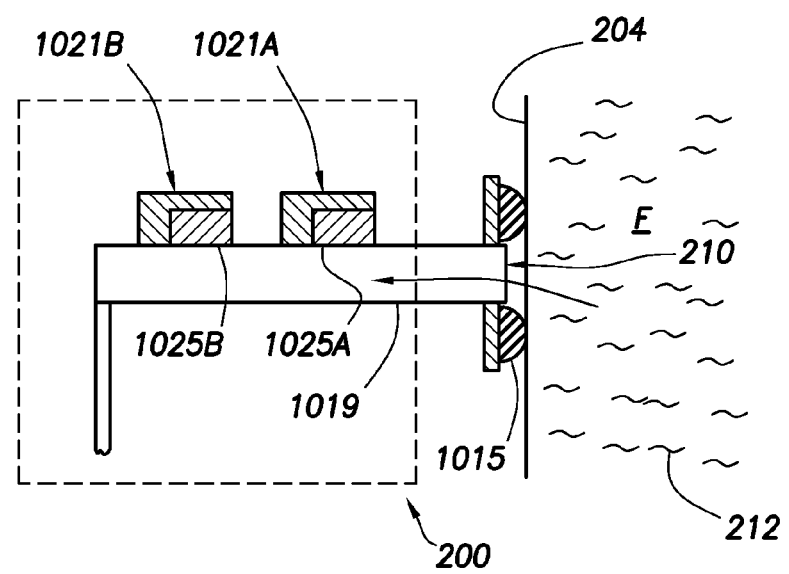

Referring now to FIG. 2B, illustrated is a schematic view of a downhole tool 200 disposed within a borehole 204 of a subterranean formation F in accordance with one or more aspects of the present disclosure. The downhole tool 200, similar to the tool shown in FIG. 2A, may include donut shaped seal 1015 provided with the probe 210, in which the seal 1015 may be used to selectively seal off a portion of the wall of the borehole 204. The tool 200 may be used to have fluid 212 drawn from the subterranean formation F into the tool 200. Accordingly, fluid 212 may be drawn through a flow line 1019 within the tool 200, using, for example, a pumping system (not shown) fluidly coupled to the tool 200.

The tool 200 may include one or more corrosion sensors 1021 coupled thereto. The tool 200 may include a first corrosion sensor 1021A and a second corrosion sensor 1021B, in which both of the corrosion sensors 1021A and 1021B may be coupled to the downhole tool 200 adjacent to the flow line 1019. The corrosion sensors 1021 may be used to quantify a corrosive strength of the fluid 212 drawn into the flow line 1019, such as by measuring an effect of corrosion by the fluid 212. As such, the downhole tool 200 may include one or more materials coupled between the corrosion sensors 1021 and the tool 200. For example, in FIG. 2B, a first material 1025A, such as a first metal alloy, may be disposed adjacent to the flow line 1019 such that the fluid within the flow line 1019 is in contact with the first material 1025A, and a second material 1025B, such as a second metal alloy, may be disposed adjacent to the flow line 1019 such that the fluid within the flow line 1019 is also in contact with the second material 1025B. The corrosion sensor 1021A may be electrically coupled to the first material 1025A and the corrosion sensor 1021B may be electrically coupled to the second material 1025B. The corrosion sensors 1021A and 1021B may be used to measure an effect of corrosion of the materials 1025A and 1025B, respectively, by the fluid 212. For example, the corrosion sensors 1021A and 1021B may be used to determine which of the materials 1025A and 1025B may be more resistant to the fluid 212. Accordingly, one or more corrosion sensors within a downhole tool may be used to monitor the corrosion of one or more components used in oilfield operations, such as the effect of corrosion of metal alloys used in completion equipment, by fluid other than fluid usually present within a borehole, such as formation fluid.

Additionally, determination of corrosive strength or corrosivity of a fluid drawn from a particular zone within a subterranean formation may be used to assert the economical value of exploiting this particular formation, or this particular zone of the subterranean formation. For example, exploitation of a zone having corrosive fluids may be less economically attractive. Based on the economical value of exploitation of the formations already traversed by the borehole, and the cost associated to further drill, a decision as to continue drilling may be taken.

Figure 3:
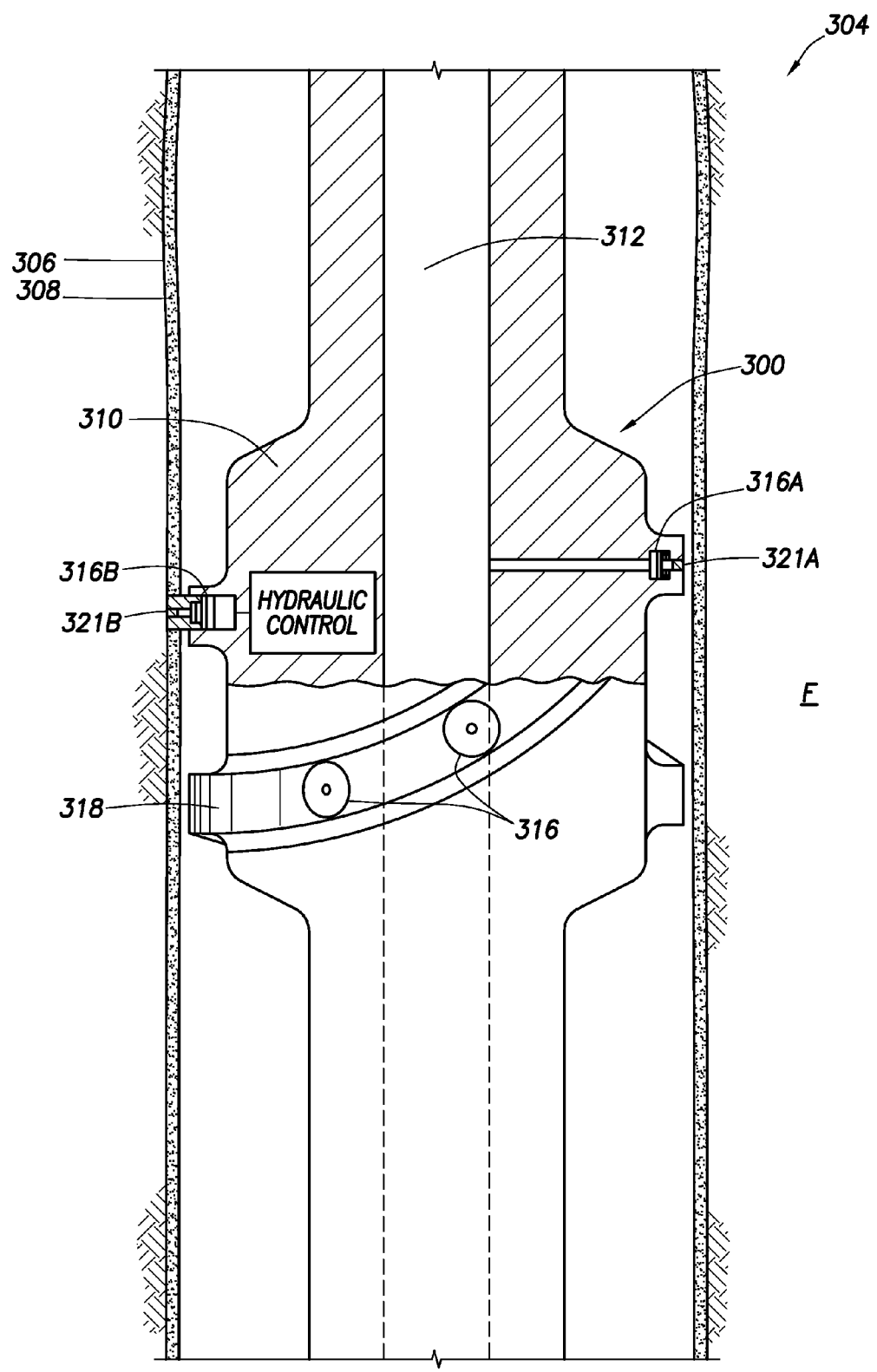
FIG. 3 is a schematic view of apparatus according to one or more aspects of the present disclosure.

Referring now to FIG. 3, a schematic view of a tool 300 in accordance with one or more aspects of the present disclosure is shown. The tool 300 may be connected to and/or included within a bottom hole assembly, in which the tool 300 may be disposed within a borehole 304 formed within a subterranean formation F.

As shown, the tool 300 may be formed as a modified stabilizer collar 310, similar to a stabilizing collar as described in FIG. 1A, and may have a passage 312 formed therethrough for drilling fluid. The flow of the drilling fluid in the passage 312 through the tool 300 may create an internal pressure $P_I$, and the exterior of the tool 300 may be exposed to an annular pressure $P_A$ of the surrounding borehole 304. A differential pressure $P_\delta$ formed between the internal pressure $P_I$ and the annular pressure $P_A$ may then be used to activate one or more draw down probes 316 included within the tool 300. For example, activation of draw down probe devices may be performed as described in U.S. Pat. No. 6,986,282, filed on Feb. 18, 2003, entitled "Method and Apparatus for Determining Downhole Pressures During a Drilling Operation," and incorporated herein by reference.

For example, the tool 300 may include draw down probes 316A and 316B that may be disposed on stabilizer blades 318 formed on the stabilizer collar 310. The draw down probe 316A may be retracted within stabilizer blades 318, and/or may be positioned in engagement with a wall 306 of the borehole 304. As shown in FIG. 3, the draw down probe 316A is not in engagement with the borehole wall 306. However, the differential pressure $P_\delta$ may be used to move the draw down probe 316A into engagement with the borehole wall 306, such as by using a hydraulic control disposed within the tool 300. As also shown in FIG. 3, the draw down probe 316B may be extended from the stabilizer blade 318, such as by using a hydraulic control disposed within the tool 300. When extended from the stabilizer blade 318, the draw down probe 316B may establish sealing engagement with the wall 306 of the borehole 304 and/or a mudcake 308 of the borehole 304. Other controllers and circuitry, not shown, may be used to couple the draw down probes 316 and/or other components of the tool 300 to a processor and/or a controller. This processor and/or controller may then be used to communicate the measurements from the tool 300 to other tools within a bottom hole assembly or to the surface of a wellsite.

The piston inside the draw down probes 316 may be retracted such that fluid may be drawn into the cavities of the draw down probes 316. For example, the draw down piston of the probe 316A may be retracted to have fluid drawn from the borehole 304 into the cavity of the draw down probe 316A, and the draw down piston of the probe 316B may be retracted to have fluid drawn from the formation F into the cavity of the draw down piston 316B.

One or more corrosion sensors 321 may then be coupled to and/or included with the draw down probes 316. As such, the corrosion sensor 321A may be disposed adjacent to the cavity in the draw down probe 316A, and the corrosion sensor 321B may be disposed adjacent to the cavity in the draw down probe 316B. The corrosion sensors 321 may be used to determine and/or measure an effect of corrosion of portions of the downhole tool 300 and/or on other metallic material samples provided with the corrosion sensors 321 by the fluid drawn into the draw down probe cavities. Fluid drawn into the cavities with the draw down pistons of the probe 316 is expected to be relatively stagnant. Drawing fluid within a cavity may be useful to reduce any artifacts that may be caused by flow of drilling fluid and/or the presence of cuttings in the fluid, such as when measuring with the corrosion sensor 321A, and/or may permit fast extraction of a fluid sample from the formation fluid, such as when measuring with the corrosion sensor 321B. After the corrosion sensors 321 have measured the corrosion effect by the respective fluids, the fluid may then be expulsed from the cavities with the draw down pistons in the probe 316 such that another measurement may be taken with the corrosion sensors 321.

Figure 4:
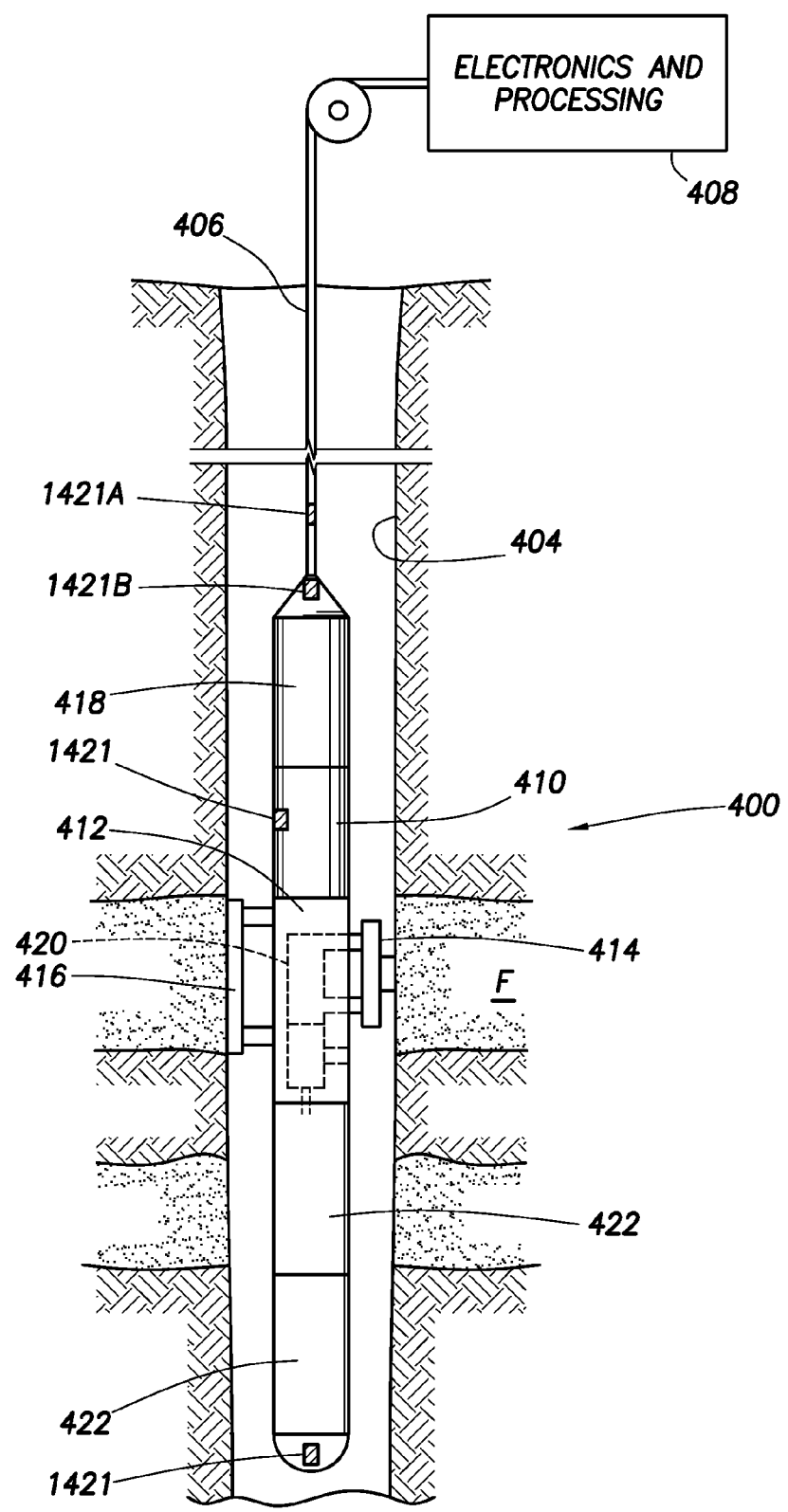
FIG. 4 is a schematic view of apparatus according to one or more aspects of the present disclosure.

Referring now to FIG. 4, a schematic view of a tool 400 in accordance with one or more aspects of the present disclosure is shown. The tool 400 may be a "wireline" tool, in which the tool 400 may be suspended within a borehole 404 formed within a subterranean formation F. The tool 400 may be suspended from an end of a multi-conductor wireline cable 406, such as by having the multi-conductor wireline cable 406 spooled around a winch (not shown) disposed on the surface of the Earth. The multi-conductor wireline cable 406 may couple the tool 400 with an electronics and processing system 408 disposed on the surface.

The tool 400 may have an elongated body 410 that includes a formation tester 412 disposed therein. The formation tester 412 may include an extendable probe 414 and an extendable anchoring member 416, in which the probe 414 and anchoring member 416 may be disposed on opposite sides of the body 410. One or more other components 418, such as a formation evaluation device, may also be included within the tool 400.

The probe 414 may be included within the tool 400 such that the probe 414 may be able to extend from the body 410 and then selectively seal off and/or isolate selected portions of the wall of the borehole 404. This may enable the probe 414 to establish pressure and/or fluid communication with the subterranean formation F to draw fluid samples from the subterranean formation F. The tool 400 may also include a fluid analysis tester 420 that is in fluid communication with the probe 414, thereby enabling the fluid analysis tester 420 to measure one or more properties of the fluid samples. The fluid samples may also be sent to one or more sample chambers or bottles 422, which may receive and retain fluids obtained from the subterranean formation F for subsequent testing after being received at the surface. The fluid from the probe 414 may also be sent back out into the borehole 404 or subterranean formation F.

Accordingly, it is contemplated to incorporate one or more of the tools and/or other devices shown in FIG. 4 with one or more aspects of the present disclosure. For example, as shown in FIG. 4, the tool 400 may include one or more corrosion sensors 1421, in which the corrosion sensors 1421 may be coupled to multiple locations of the downhole tool 400. For example, as shown, some of the corrosion sensors 1421 may be disposed upon the body of the downhole tool 400, and/or coupled to the wireline cable 406 of the downhole tool 400. The corrosion sensor 1421A may be used to measure an effect of corrosion of metallic components in the wireline cable 406 by the drilling fluid in the borehole 404. Similarly, the corrosion sensor 1421B, while disposed at the head of the wireline tool 400, may also be used to measure an effect of corrosion metallic components in the wireline cable 406 of the tool. Additionally and/or alternatively, the fluid analysis tester 420 and/or the sample chambers 422 may include one or more corrosion sensors, similar to FIG. 2B, to measure corrosion by fluid extracted from the formation F with the tool 400.

As such, potential locations for one or more corrosion sensors are shown for a wireline tool. The corrosion sensors, thus, may be used to monitor and measure the corrosion of the housing of the wireline tool 400, and/or may be used to monitor and measure the corrosion of the wireline cable 406. To transmit measurements to the electronic and processing unit 408, the sensors 1421 may be communicatively coupled to the wireline cable 406.

Figure 5:
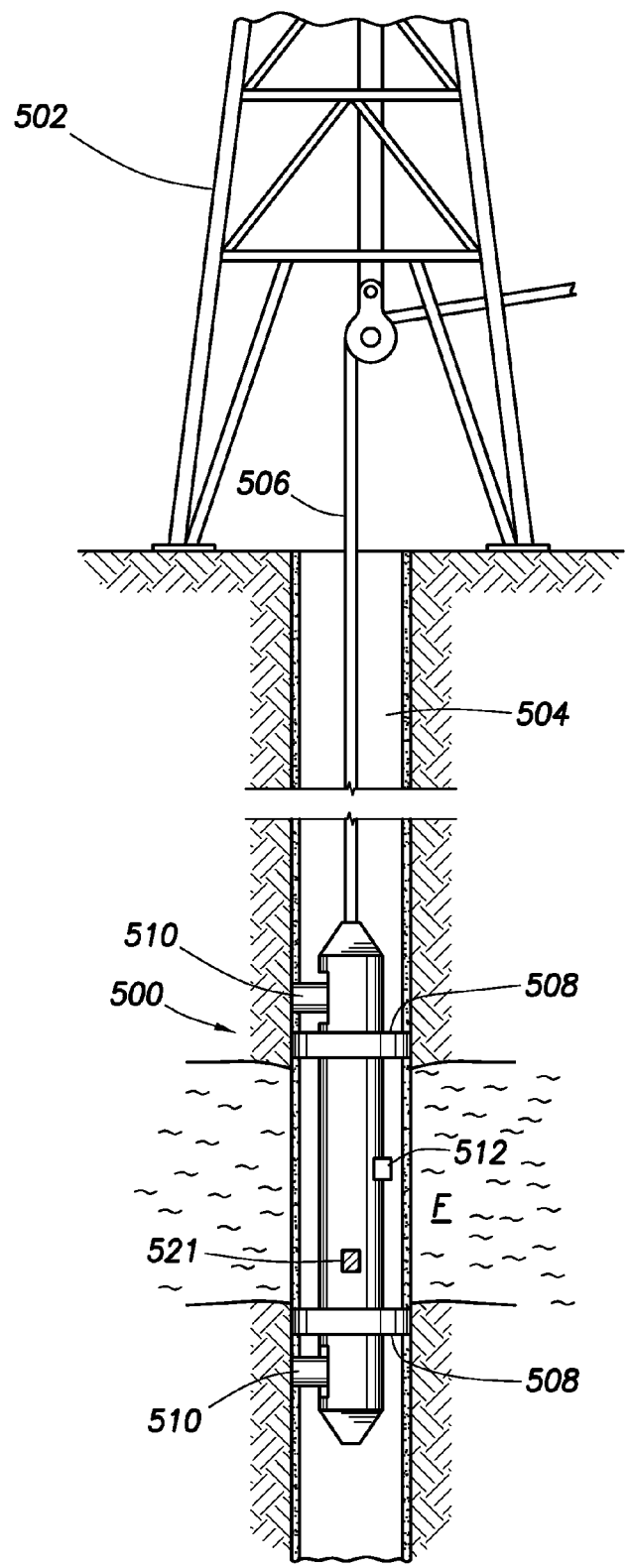
FIG. 5 is a schematic view of apparatus according to one or more aspects of the present disclosure.

Referring now to FIG. 5, a schematic view of another tool 500 in accordance with one or more aspects of the present disclosure is shown. Similarly to FIG. 4, the tool 500 may be suspended within a borehole 504 formed within a subterranean formation F using a multi-conductor wireline cable 506. The multi-conductor wireline cable 506 may be supported by a drilling rig 502.

As shown, the tool 500 may include one or more packers 508 that may be configured to inflate, thereby selectively sealing off a portion of the borehole 504 around the tool 500, and between the tool 500 and the subterranean formation F. To test the subterranean formation F, the tool 500 may include one or more probes 510, and the tool 500 may also include one or more outlets 512 that may be used to inject fluids within the borehole portion sealed off by the packers 508. For example, the tool 500 may be used to inject fracturing fluid including hydrogen chloride.

Accordingly, some injection fluid disposed within the tool 500 may corrode portions of the tool 500. As such, one or more corrosion sensors 521 may be included within the tool 500, such as by having a corrosion sensor 521 located in the injection interval to monitor the corrosion of the housing of the tool 500 by the injection fluid. This may enable a surface operator to be alerted if excessive corrosion is detected by the corrosion sensor 521.

Figure 6:
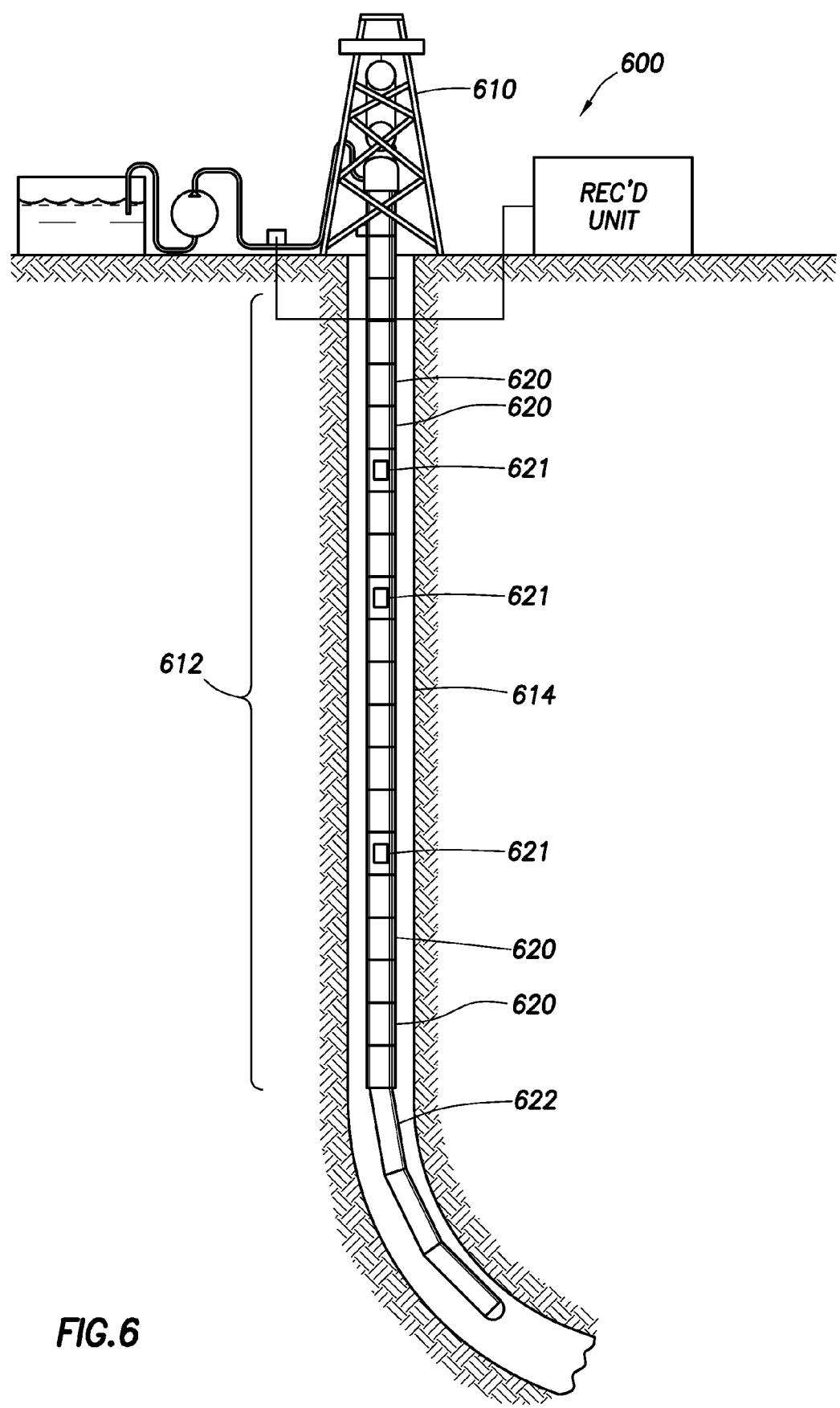
FIG. 6 is a schematic view of apparatus according to one or more aspects of the present disclosure.

Referring now to FIG. 6, a schematic view of a wellsite 600 having a drilling rig 610 in accordance with one or more aspects of the present disclosure is shown. A borehole 614 may be formed within a subterranean formation F, such as by using a drilling assembly, or any other method known in the art. A wired pipe string 612 may also be suspended from the drilling rig 610. The wired pipe string 612 may be extended into the borehole 614 by threadably coupling together multiple segments 620 (i.e., joints) of wired drill pipe in an end-to-end fashion. For example, the wired drill pipe segments 620 may be similar to wired drill pipe segments described in U.S. Pat. No. 6,641,434, filed on May 31, 2002, entitled "Wired Pipe Joint with Current-Loop Inductive Couplers," and incorporated herein by reference.

Wired drill pipe may be structurally similar to a typical drill pipe, however the wired drill pipe may additionally include a cable installed therein to enable communication through the wired drill pipe. The cable installed within the wired drill pipe may be any type of cable capable of transmitting data and/or signals therethrough, such an electrically conductive wire, a coaxial cable, an optical fiber cable, and or any other cable. The wired drill pipe may include a form of signal coupling, such as inductive coupling, to communicate data and/or signals between adjacent pipe segments 620 when assembled together.

A string of multiple borehole tools 622 may be coupled to a lower end of the wired pipe string 612. The tools 622 may include one or more tools used within wireline applications, may include one or more LWD tools, may include one or more formation evaluation or sampling tools, and/or may include any other tools capable of measuring a characteristic of the subterranean formation F.

The tools 622 may be connected to the wired pipe string 612 during or shortly after drilling the borehole 614, such as by pumping or otherwise moving the tools 622 down the wired pipe string 612 while still within the borehole 614. If installed after drilling the borehole 614, the tools 622 may be connected to the lower end of the wired pipe string 612 and the string 612 may be extended into the borehole 614 by adding drill pipe segments 620. The tools 622 may then be positioned within the borehole 614, as desired, through the selective movement of the wired pipe string 612, in which the tools 622 may gather measurements and data. These measurements and data from the tools 622 may then be transmitted to the surface of the borehole 614 using the cable within the wired drill pipe 612.

One or more corrosion sensors 621 may be disposed along the wired pipe string 612, such as by having the corrosion sensors 621 coupled to repeaters within the wired pipe string 612. The data and measurements taken and collected by the corrosion sensors 621 (and any components coupled thereto) may then be transmitted to the surface using the wired pipe string 612. Corrosion by the drilling mud may be monitored by a plurality of corrosion sensors 621. A difference of the two measurements may represent the change of corrosion by the drilling mud due to change of drilling mud temperature, pressure and/or due to the flow of formation fluids and/or gases into the borehole 614 at various places along the borehole 614. Thus, the corrosion sensors may be used to detect an occurrence and/or a position of flow of formation fluids and/or gases into the borehole 614.

Figure 7:
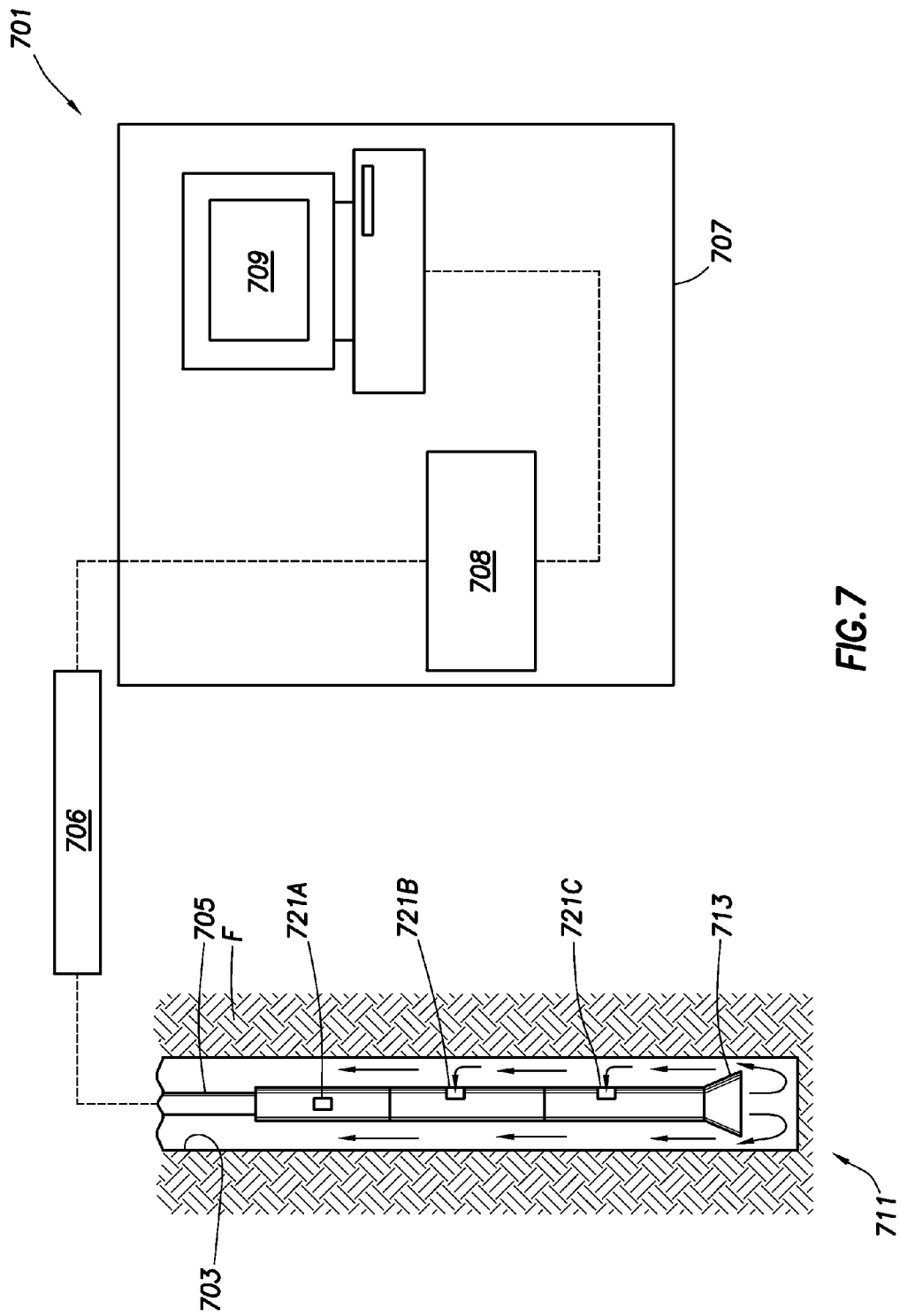
FIG. 7 is a schematic view of apparatus according to one or more aspects of the present disclosure.

Referring now to FIG. 7, a schematic view of a system 701 having a bottom hole assembly ("BHA") 711 in accordance with one or more aspects of the present disclosure is shown. The BHA 711 may be disposed within a borehole 703 formed within a subterranean formation F, in which the BHA 711, as shown, may be used to form the borehole 703 within the subterranean formation F. For example, the BHA 711 may be coupled to a wired drill pipe string 705 and may include a drill bit 713 attached to a distal end thereof. The BHA 711 may have a passage formed therethrough (not shown), in which drilling fluid may be pumped from the surface of the subterranean formation F, through the wired drill pipe string 705, and then exit from the BHA 711 through one or more ports formed within the drill bit 713. The fluid may then flow back upwardly through the borehole 703, such as through the annulus formed between the drilling string 705 and the borehole 703, the fluid flow being indicated generally by direction arrows.

Corrosion sensors may be used in the BHA 711, and may be configured to measure an effect of corrosion of a portion of metal material, such as a portion of BHA housing, by a fluid, such as the drilling fluid. In other words, a corrosion sensor, in accordance with the present disclosure, may be used to measure the corrosive strength of the drilling fluid, such as to be able to measure an effect indicating corrosion of a portion the BHA 711 by the drilling fluid.

For example, the BHA 711 may include three corrosion sensors 721A, 721B, and 721C, as shown; however, those having ordinary skill in the art will appreciate that a tool in accordance with the present disclosure may have only one corrosion sensor coupled thereto, or may include multiple corrosion sensors coupled thereto. The corrosion sensor 721A may be disposed in fluid communication with an inner bore of the BHA 711, such as disposed adjacent to the drilling fluid passage formed within the BHA 711. The corrosion sensor 721A may be able to measure an effect of corrosion of a metallic portion of the BHA 711 by the drilling fluid flowing through the passage in the BHA 711. The corrosion sensors 721B and 721C may be disposed in fluid communication with an annulus of the borehole 703, such as on the outer surface of the BHA 711. For example, as shown, the corrosion sensor 721B may be disposed at a first axial location on the BHA 711, and the corrosion sensor 721C may be disposed at a second axial location on the BHA 711, thereby having the corrosion sensor 721B disposed axially above the corrosion sensor 721C with respect to the borehole 703. As such, this arrangement may enable the corrosion sensors 721B and 721C to measure the properties of the drilling fluid as the drilling fluid flows upwards within the borehole 703. Those having ordinary skill in the art will appreciate that, though the corrosion sensors are disposed at particular locations, one or more of the corrosion sensors may be disposed at any location with respect to a bottom hole assembly such that the corrosion sensors may be able to measure an effect of corrosion.

The measurements taken by the corrosion sensors may be compared with each other, such as by comparing the measurements of the inner corrosion sensors 721A with the measurements of the outer corrosion sensors 721B and/or 721C. A comparison of the measurement of the corrosion sensors 721 may facilitate determining if gas and/or fluid from the subterranean formation F is being introduced in the borehole 703, and may also facilitate determining the corrosion effect upon the BHA 711 at different locations. Additionally, one or more corrosion sensors may be included up hole, such as on the surface of the drilling rig shown in FIG. 1A, for example within and/or adjacent to the pipes of the pit 130 in FIG. 1A. This may enable monitoring of fluids going into the borehole, fluids within the borehole, and fluids coming out of the borehole and measure the effect of corrosion of the BHA 711 and/or its components.

Referring still to FIG. 7, the system 701 may include a telemetry unit 706 and a surface unit 707. The telemetry unit 706 may be coupled to one or more of the corrosion sensors 721, in which the telemetry unit 706 may be used to transmit the measured effect of corrosion measured by the corrosion sensors 721 to the surface unit 707. The telemetry unit 706 may be part of the BHA 711 and/or may be coupled to the BHA 711, in which the telemetry unit 706 may include one or more communication components to transmit a signal to the surface unit 707. For example, the telemetry unit 706 may include a wired drill pipe telemetry unit to transmit a signal through wired drill pipe 705 to the surface unit 707. In this example, the monitoring and measuring of corrosion may be enhanced using a high data rate provided by wired drill pipe 705 and may permit early detection of formation fluid and/or gases influx into the borehole 703, as well as rapid detection of corrosion of the components in the BHA 711 by the drilling fluid and/or the mixture of drilling fluid and formation fluid or gases. However, the telemetry unit 706 may include any other telemetry components and/or devices known in the art or future-developed to transmit a signal to the surface unit.

The surface unit 707 may include a receiver 708 that may be used to receive the measurements of the corrosion sensors 721, the receiver 708 being communicatively coupled to a control system 709 that may optionally, but not necessarily, be included in the surface unit 707. The control system 709 may be configured to analyze and examine the measured effect of corrosion, and then, based on the analysis or examination, the control system 709 may alert a user, such as providing the user with warnings. For example, warnings may indicate whether corrosion measurements are within a predetermined range deemed acceptable for the BHA 711, and/or whether corrosion measurements are out of the predetermined range deemed unacceptable for the BHA 711. Further, based upon the measured corrosion effect, the composition of the drilling fluid introduced in the borehole 703 may be modified, such as by adding one or more components to the drilling fluid, thereby adjusting the corrosion effect.

Figure 9:
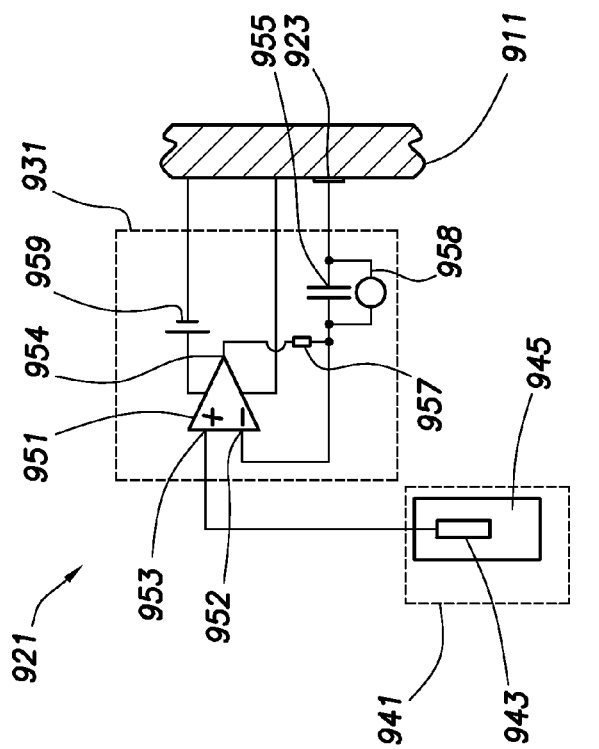
FIG. 9 is a schematic view of apparatus according to one or more aspects of the present disclosure.

A corrosion sensor used in accordance with the present disclosure may include an electrochemical corrosion transducer. In FIG. 9, a corrosion sensor 921 is shown as an electrochemical corrosion transducer. However, those having ordinary skill in the art will appreciate that, although an electrochemical corrosion transducer is described in FIG. 9, any corrosion sensor known in the art or future-developed may be used with a downhole tool in accordance with one or more aspects of the present disclosure.

The corrosion sensor 921 may be configured to be disposed within a borehole. For example, the corrosion sensor is coupled to a metal material 911, and the metal material 911 may be configured to be exposed to a downhole fluid. The corrosion sensor 921 may be used to determine an indication of dissolution or oxidation of the metal material 911 by the downhole fluid. Also, the corrosion sensor 921 may be used to a quantifying the corrosive strength of the downhole fluid on the metal material 911. The corrosion sensors 921 may be configured to measure an electrical potential difference (e.g., voltage) between two electrodes made of similar or identical materials. The electrodes may include a reference electrode and a working electrode, in which the reference electrode is exposed to a preselected fluid, or a known fluid, and the working electrode is exposed to the downhole fluid that is to be characterized.

The corrosion sensor 921 may include an electrical contact 923, an electronics unit 931, and an electrochemical cell 941. The electrical contact 923 may be electrically coupled to the metal material 911, the electronics unit 931 may be electrically coupled to the electrical contact 923, and the electrochemical cell 941 may be electrically coupled to the electronics unit 931. An electrical contact used to electrically couple a portion of the corrosion sensor 921 with a metal material 911 may be any contact known in the art. For example, the electrical contact 923 may be a pressure contact, in which the pressure contact may apply pressure against the metal material to ensure an electrical coupling with the metal material. However, those having ordinary skill in the art will appreciate that other structures and arrangements may be used as an electrical contact to electrically couple the portion of the corrosion sensor with the metal material. One advantage that may be provided by the sensor 921 is that the sensor 921 may be connected to downhole equipments, such as metallic portions of downhole tool housing, via the electrical contact 923. Thus, the sensor 921 may be used to monitor an effect of corrosion of downhole equipments while leaving said downhole equipment free of additional through hole or other machining that may otherwise be needed to implement the sensor 921.

The electrochemical cell 941 may include an electrode 943 disposed within a fluid 945. As such, the electrochemical cell 941 may include a housing, in which the electrode 943 and the fluid 945 are disposed within the housing of the electrochemical cell 941. The housing material may include or be made of a chemically inert material, such as a material that does not react with the fluid 945. The electrochemical cell 941 may be maintained in good thermal contact with metal material 911 using, for example, a heat sink (not shown). For example, the housing of the electrochemical cell may be disposed adjacent to the heat sink. Thus, the temperature in the electrochemical cell 941 may be essentially equal to the temperature of the metal material 911 and/or the temperature of the downhole fluid to which the metal material 911 is exposed.

The electrode 943 of the electrochemical cell 941 may include or be made of a preselected material, such as by having the electrode 943 include a material identical or similar to the material that the metal material 911 is made of. Thus, if the metal material 911 is made of, or includes, steel, or a particular type of steel, this steel, or this particular type of steel, may be included in the electrode 943.

The fluid 945 of the electrochemical cell 941 may include or be made of a preselected fluid, such as by having the fluid 945 include a fluid similar to that to which the metal material 911 may be exposed. For example, if the metal material 911 is to be exposed to drilling fluid or formation fluid, the fluid 945 may include a preselected drilling fluid or formation fluid, respectively. Further, the selected fluid 945 may have demonstrated through laboratory experiments that the corrosion of the metal material 911 by the selected fluid 945 is acceptable within a desired or predetermined temperature range, such as the metal material 911 is suitable for downhole use in contact with the selected fluid 945, and/or such as a downhole tool including or made of metal material 911 has a suitable useful life when exposed to the selected fluid 945. Accordingly, the electrode 943 and the fluid 945 of the electrochemical cell 941 may be selected such that no reduction and/or oxidation, or a minimal amount of reduction and/or oxidation, occurs within the electrochemical cell 941 within a desired or predetermined temperature range corresponding a temperature range at which the metal material 911 is intended to be used for a particular downhole application.

The electronics unit 931 may include one or more circuits therein, in which the electronics unit 931 is electrically coupled between the electrochemical cell 941 and the electrical contact 923. The electronics unit 931 includes an operational amplifier 951, in which the operational amplifier 951 may include an inverting input 952, a non-inverting input 953, and an output 954. As shown, the electrochemical cell 941 may be electrically coupled to the non-inverting input 953 of the operational amplifier 951, and the electrical contact 923 may be electrically coupled to the inverting input 952 of the operational amplifier 951.

The electronics unit 931 may include a capacitor 955, in which the capacitor 955 may be electrically coupled between the electrical contact 923 and the inverting input 952 of the operational amplifier 951. The capacitor 955 may be electrically coupled in series with the metal material 911 through the electrical contact 923 and the inverting input 952 of the operational amplifier 951. The electronics unit 931 may also include a feedback loop formed therein, such as by including an impedance (e.g., a resistor) 957 electrically coupled between the output 954 of the operational amplifier 951 and the inverting input 952 of the operational amplifier 951. For example, as shown, the resistor 957 may be electrically coupled to the inverting input 952 of the operational amplifier 951 before the capacitor 955 is electrically coupled to the inverting input 952 of the operational amplifier 951. This may enable an electrical potential difference (e.g., voltage) formed across the capacitor 955 to be similar to the difference between the redox potential of the electrochemical cell 941 and the redox potential of a chemical cell formed by the metal material 911 exposed to the downhole fluid.

The electronics unit 931 may further include a voltmeter 958 therein, in which the voltmeter 958 may be electrically coupled across the capacitor 955. This may enable the voltmeter 958 to measure the electrical potential difference across the capacitor 955, thereby enabling the voltmeter 958 to measure the electrical potential difference between the electrochemical cell 941 and the electrode made of the metal material 911 through the electrical contact 923. The electronics unit 931 may include a power supply therein, such as a battery 959, as shown, in which the power supply may be electrically coupled to the operational amplifier 951 of the electronics unit 931 to supply power thereto. As shown by the arrangement in FIG. 9, current drawn and/or generated by the operational amplifier 951 may be returned to the metal material 911.

Those having ordinary skill in the art will appreciate that, though the electronics unit 931 is shown in FIG. 9 having a particular arrangement for an electrical circuit, other arrangements and/or other circuits may be used for implementing the electronics unit 931 without departing from the scope of the present disclosure.

In operation, the electrical potential difference may be measured between the electrochemical cell 941, such as a reference electrode having a first electrical potential, and the electrical contact 923 and the metal material 911 exposed to the fluid, such as a working electrode having a second electrical potential. In contrast with known electrochemical sensors that are configured to determine a concentration of oxidizing agent, this measured electrical potential difference may indicate an effect of corrosion of the metal material 911 when exposed to the fluid. For example, in operation, the sign (e.g., positive or negative) of the measured electrical potential difference, such as measured by the voltmeter 958, may be used to indicate whether the fluid 945 in electrochemical cell 941 is more corrosive than the fluid to which the metal material 911 is exposed. Also, in contrast with known corrosion sensors, the measurement performed with the corrosion sensor 921 may be independent of the resistivity of the fluids.

Those having ordinary skill in the art will appreciate that the present disclosure contemplates coupling a corrosion sensor to any tool that may be used downhole and may be used to measure effect of corrosion by any fluid. For example, as above, aspects of FIG. 9 may be included within a LWD/MWD tool, as shown for example in FIG. 8.

Figure 8:
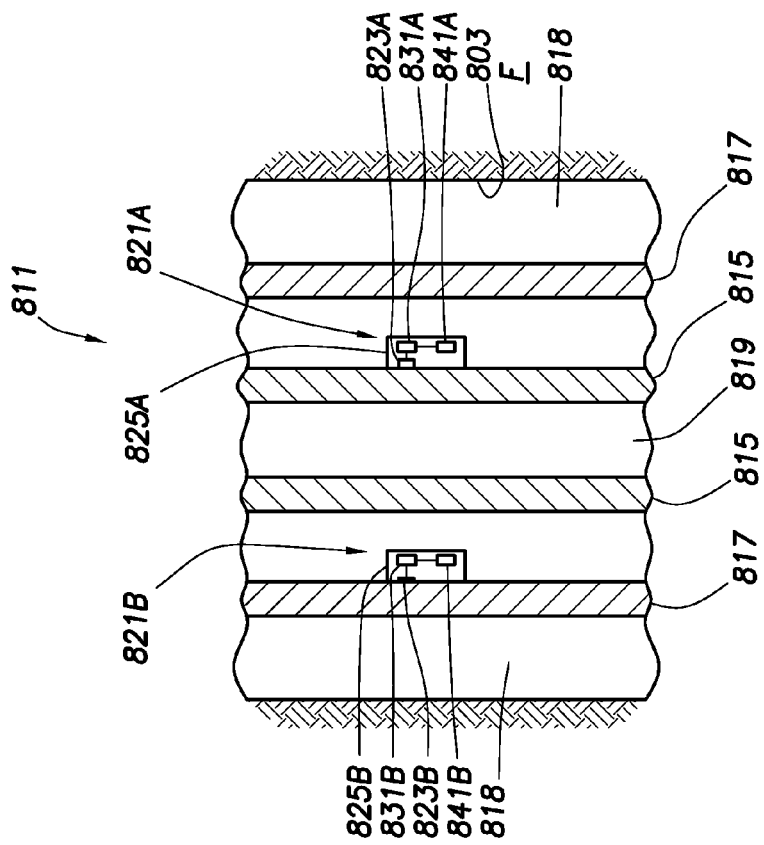
FIG. 8 is a schematic view of apparatus according to one or more aspects of the present disclosure.

Referring now to FIG. 8, a schematic view of a downhole LWD/MWD tool 811 in accordance with one or more aspects of the present disclosure is shown. As such, corrosion sensors 821 shown may be electrochemical corrosion transducers, similar to the electrochemical corrosion transducer 921 described in FIG. 9. For example, one or more of the corrosion sensors 821 may include an electrical contact 823, an electronics unit 831, and an electrochemical cell 841. Given the benefit of the present disclosure, those skilled will the art will appreciate that the corrosion sensors 821 and/or 921 may perform reliable measurements while allowing fluid (e.g., drilling fluid) to flow within the passage 819, and/or fluid (e.g., drilling fluid) to flow within the annulus 818. Also, the corrosion sensors 821 and/or 921 may be less sensitive to fouling than other types of known corrosion sensors.

As shown, the downhole tool 811 may include a first body portion 815 and a second body portion 817. The first body portion 815 of the downhole tool 811 may be, for example, a chassis, and the second body portion 817 of the downhole tool 811 may be, for example, a collar, in which the first body portion 815 may be disposed within the second body portion 817. The downhole tool 811 may include a passage 819 formed therethrough. Fluid (e.g., drilling fluid) may be able to flow within the passage 819 formed within the first body portion 815 of the downhole tool 811, and fluid (e.g., drilling fluid) may also be able to flow within an annulus 818 formed between the wall 803 of the borehole 818 and the outer surface of the second body portion 817 of the downhole tool 811.

The downhole tool 811 may include one or more corrosion sensors 821 coupled thereto. The downhole tool 811 includes two corrosion sensors 821A and 821B, in which the corrosion sensor 821A may be coupled to the first body portion 815 and the corrosion sensor 821B may be coupled to the second body portion 817. However, the corrosion sensors 821 may alternatively be coupled to a plug (not shown) configured to sit in a port provided on the body portions 815 and/or 817. The plug may comprise a volume of material identical or similar to the material making or included in the body portion 815 or 817. At least a portion of the plug surface may be exposed to the drilling fluid. In cases where the plug is surrounded by an electrical insulator, a connector may be provided across the insulator. The connector may be configured to electrically couple the sensor 821 to the volume of material identical or similar to the material making or included in the body portion 815 or 817.

The electrical contact 823 may be electrically coupled to the tool 811, such as by having the electrical contact 823A of the corrosion sensor 821A electrically coupled to the first body portion 815 of the downhole tool 811 and the electrical contact 823B of the corrosion sensor 821B electrically coupled to the second body portion 817 of the downhole tool 811. The electronics unit 831 may be electrically coupled to the electrical contact 823, such as by having the electronics unit 831A electrically coupled to the electrical contact 823A and the electronics unit 831B electrically coupled to the electrical contact 823B. The electrochemical cell 841 may also be electrically coupled to the electronics unit 831, such as by having the electrochemical cell 841A electrically coupled to the electronics unit 831A, and having the electrochemical cell 841B electrically coupled to the electronics unit 831B.

Accordingly, when using the corrosion sensors 821 as electrochemical corrosion transducers, the corrosion sensors 821 may form two or more electrodes therein such as to be able to have an electrical potential difference measured between the two electrodes. As shown, the electrochemical cell 841 of the corrosion sensors 821 may be used to form a first electrode, such as a reference electrode. The electrochemical cell 841 may include an electrode disposed within a fluid, such as a reference fluid, in which the electrochemical cell 841 may be used to establish a first electrical potential. The electrical contact 831, which is electrically coupled to the tool 811 may be used to form a second electrode, such as a working electrode. As the electrical contact 831 is electrically coupled to the body of the tool 811, a metallic portion of the body of the tool 811 that is exposed to a fluid may be used as the electrode, and the fluid exposed to the tool may be used as the working fluid. The working electrode may be formed by the metallic portion of the body of the tool 811 and the fluid flowing across the surface of the tool 811. For example, in FIG. 8, the working electrode of the sensor 821A may be formed with the first body portion 815 of the downhole tool 811, and the first body portion 815 may be exposed to fluid flowingly through the passage 819 of the downhole tool 811. Also in FIG. 8, the working electrode of the sensor 821B may be formed with the second body portion 817 of the downhole tool 811, and the second body portion 817 may be exposed to fluid flowingly through the annulus 818. The working electrodes may then be used to establish a second electrical potential.

The corrosion sensors 821 may be configured to maintain a substantially uniform temperature therein and/or maintains a good thermal contact between the corrosion sensors 821A and 821B and the body 815 and 817, respectively. For example, the corrosion sensor may include a heat sink 825 to enable the electrochemical cell 841A and the body 815 and/or the electrochemical cell 841B and the body 817 to be maintained at essentially the same temperature. For example, the electrochemical cell 841 may be disposed adjacent to and/or coupled to the heat sink 825, in which the heat sink 825 may then be disposed adjacent to and/or coupled to the downhole tool 811 (e.g., to the body 815 and/or 817 of the downhole tool 811).

The electrical potential difference may be measured between the first electrical potential (formed by the electrochemical cell 841, such as a reference electrode) and the second electrical potential (formed by the electrical contact 831, such as a working electrode), in which the corrosion sensors 821 may be used to measure and/or determine an effect of corrosion from the measured electrical potential difference. For example, the corrosion sensor 821A may be used to measure an effect of corrosion of the first body portion 815 by the fluid within the passage 819, and the corrosion sensor 821B may be used to measure an effect of corrosion of the second body portion 817 by the fluid within the annulus 818.

In operation, the electrical potential differences measured by the sensors 821 may be indicative of whether the actual drilling fluid is more oxidizing than the reference fluids in the electrochemical cells 841, and by how much. The electrical potential difference measured with the sensors 821 may be transmitted up hole to a surface operator, for example using Wired Drill Pipe. Alternatively, only the sign of the potential difference may be transmitted up hole.

In cases where the reference fluids include samples of drilling fluid for which the body portions 815 and 817 have been qualified, that is, the corrosion of the body portions 815 and/or 817 by the respective samples of drilling fluid is deemed acceptable, the electrical potential differences measured by the sensors 821 may indicate whether the corrosion of body portions 815 and 817 in the current drilling fluid is faster or more intense than the corrosion of body portions 815 and 817 in the samples of drilling fluid for which the body portions 815 and 817 have been qualified. Thus, the sign of the electrical potential differences measured by the sensors 821 may also be indicate whether the corrosion of the body portions 815 and/or 817 by the actual drilling fluid may be considered acceptable.

While FIG. 8 relates to LWD/MWD tools having aspects of FIG. 9 included therein, the aspects of FIG. 9 may be included within other tools, such as a sampling tool. For example, one or more corrosion sensors similar to the sensors 921 may be used in a sampling tool, such as shown in FIGS. 2A and 2B, to determine if formation fluid pumped from the subterranean formation is more oxidizing, and therefore more corrosive, than a sample of formation fluid for which a metal alloy used in completion equipment has been qualified. In such cases, a corrosion sensor may have an electrochemical cell, in which an electrode within the electrochemical cell may be similar to that of a metal alloy used in completion equipment. A fluid within the electrochemical cell may be a preselected fluid that may provide limited corrosion of the metal alloy. For example, laboratory measurements may have demonstrated that the life of the metal alloy in presence of the preselected fluid is acceptable in a temperature range corresponding expected formation fluid temperatures or temperature range at which the metal alloy is intended to be used.

Referring back to FIG. 2B, first and second corrosion sensors 1021A and 1021B may have first and second electrochemical cells, in which first and second electrodes within the first and second electrochemical cells may be similar to first and second metal alloys 1025A and 1025B used in completion equipment, respectively. However, more than two corrosion sensors and associated metal alloys sensors may be used within the scope of the present disclosure. For example, the second metal alloy 1025B may be more resistant to corrosion than the first alloy 1025A. First and second fluids within the first and electrochemical cells may be preselected fluids that may affect suitable corrosion of the first and second electrodes by the first and second preselected fluids, respectively. Typically, the second fluid may be more oxidizing or corrosive than the first fluid. In operation, the sign (and optionally the magnitude) of the voltage measurements performed by the first and second corrosion sensors 1021A and 1021B may indicate whether both first and second metal alloys may be used in completion equipment with the formation fluid, whether only the second metal alloy (more resistant) may be used, and whether none of the first and second alloys may be used.

As an alternative, the present disclosure contemplates providing a direct measurement of corrosion effect with the use of anodic stripping voltammetry ("ASV"). Turning now to anodic stripping voltammetry and its implementation within down-hole measurement systems, and/or conveyance cables, a metal (e.g, tool body metal, completion metal sample, etc) corrodes and liberates ions in a downhole fluid (drilling fluid, fracturing fluid, or fluid pumped from the formation). A concentration of one or more liberated ions in the downhole fluid may be monitored using anodic striping voltammetry (ASV). Corrosion by the downhole fluid is determined based on concentration levels and/or level variations. The corrosion monitoring may be performed in-situ and may permit the withdrawal of the tool before excessive corrosion results in failure, and optionally, may also permit the replacement of the parts with alternate materials.

Figure 10A:
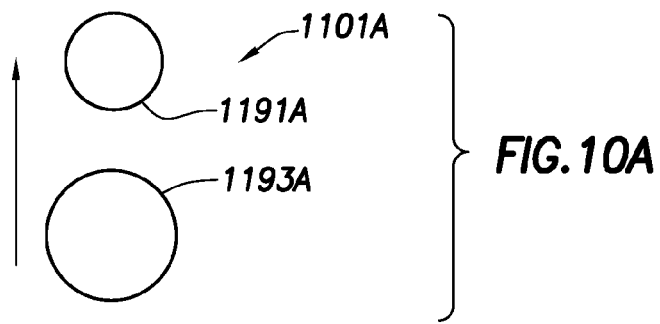
FIGS. 10A, 10B, and 10C are schematic views of apparatus according to one or more aspects of the present disclosure.
Figure 10B:
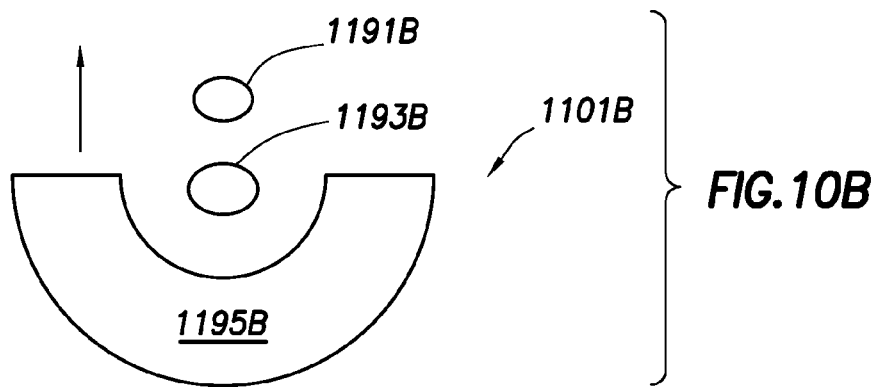
Figure 10C:
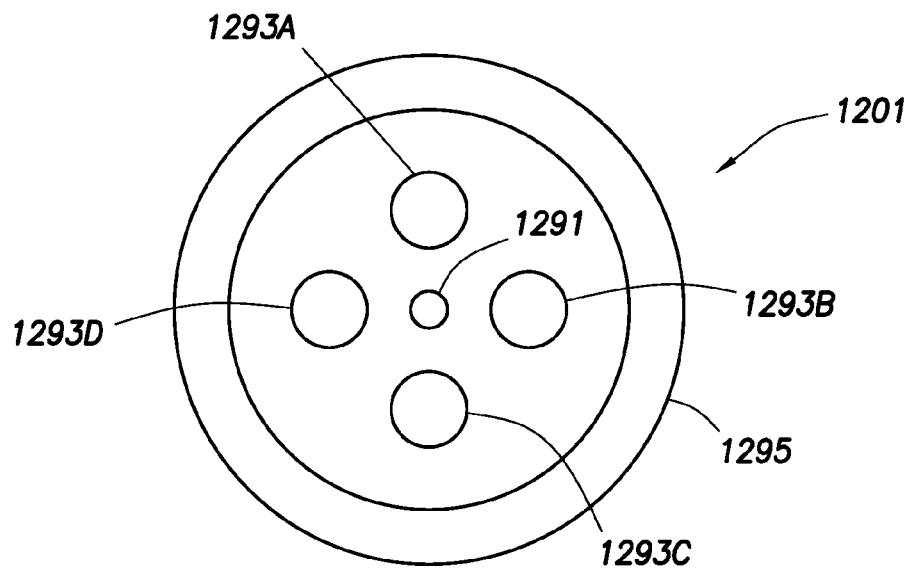

The anodic stripping voltammetry may be conducted with electrochemical corrosion transducers having two electrodes, such as shown in FIG. 10A, three electrodes, such as shown in FIG. 10B, and/or more electrodes, such as shown in FIG. 10C. An array of electrodes, as shown on FIG. 10C, may be used when multiple ionic concentrations are measured with anodic stripping voltammetry. The electrodes may include at least one working electrode and a reference electrode, and may further include an auxiliary electrode. The working electrode may be used to generate an electroplating reaction, such as to have one or more ionic species deposited on the working electrode, and may be used to generate an oxidation reaction, such as to have one or more ionic species stripped, at least partially, from the working electrode. The depositing and stripping of the one or more ionic species to the working electrode may be generated by varying an electrical potential difference between the working electrode and the reference electrode.

The auxiliary electrode, if used, and also often referred to as a counter electrode, may be substantially maintained at the same or similar electrical potential as that of the reference electrode. The auxiliary electrode may be used to pass current to the working electrode, thereby minimizing an affect to the electrical potential of the reference electrode. The electrical current may then be measured between the working electrode and the auxiliary electrode, if the auxiliary electrode is present, or may be measured the working electrode and the reference electrode otherwise. One or more of the electrodes may include and/or be made of an inert material, such as platinum, glass fiber, carbon fiber, and/or gold. Alternatively, one or more of the electrodes may include a carbon paste-based ion-selective dual function microelectrode, such as used within a scanning electrochemical microscope.

An electrochemical corrosion transducer only having two electrodes, such as a working electrode and a reference electrode, as shown in FIG. 10A, may require a larger surface area and/or a larger solid-liquid interface for the electrodes as compared to an electrochemical corrosion transducer having three or more electrodes, such as a working electrode, a reference electrode, and an auxiliary electrode, as shown in FIG. 10B. The electrodes may be of any size, but for reliability purposes when using anodic stripping voltammetry, particularly when using fast-scan anodic stripping voltammetry and/or fast-scan cyclic voltammetry, diameters for the solid-liquid interface of an electrode of about 100 μm micrometers (about 0.0039 inches) and smaller may be desired. As such, when smaller sizes are used for an electrode, an auxiliary electrode may be desired, as the surface area for the solid-liquid interface of the auxiliary electrode may be larger than the surface area for the solid-liquid interface of the working electrode and/or the reference electrode.

When using anodic stripping voltammetry, one or more species are electroplated on to the working electrode. One or more ionic species may be oxidized (stripped) at least partially from the working electrode in the medium found downhole. When stripping one or more ionic species from the working electrode, an electrical potential difference between the working electrode and the reference electrode may be varied, by varying the magnitude of the electric potential of the working electrode with respect to the reference electrode. The electrical current drawn at the working electrode, or the electrical current between the working electrode and the auxiliary electrode (if present), is measured during the stripping of the one or more ionic species. The electrical current is measured as a function of the measured electrical potential difference between the working electrode and the reference electrode, and measured as a function of time.

As such, in accordance with one or more aspects of the present disclosure, a method to measure one or more properties of a solution using anodic stripping voltammetry may include biasing the electrical potential difference between a working electrode and a reference electrode such that electroplating of one or more ionic species from the solution on the working electrode occurs, thereby depositing one or more ionic species from the solution on the working electrode. This may be achieved, for example, by applying a predetermined constant negative bias to the working electrode that may be applied for a predetermined time (such as within on the order of a second).

After biasing the electrical potential difference between the working electrode and the reference electrode, the bias between the electrical potential difference between the working electrode and the reference electrode may be altered enabling one or more ionic species deposited on the working electrode to be stripped, at least partially, from the working electrode. Altering the bias of the electrical potential difference may be achieved by varying the electrical potential difference between the working electrode and the reference electrode. The electrical potential difference may be increased linearly, or through a staircase function, or a square-wave function, or a pulse function, or any other function found desirable. To determine the presence of multiple ionic species within the solution (and therefore stripped away from the working electrode) fast-scan anodic stripping voltammetry and/or fast-scan cyclic voltammetry may be used. As such, fast-scan anodic stripping voltammetry and/or fast-scan cyclic voltammetry may be performed so that the variation rate of the electrical potential difference with respect to time may be performed up to about 100 $V \cdot s^{-1}$ volts per second.

As the electrical potential difference between the working electrode and the reference electrode is varied, the electrical current drawn at the working electrode is measured relative to either the reference or if present the auxiliary electrode. The electrical current may be measured as a function of the measured electrical potential difference and as a function of time. This may enable the oxidation (e.g., stripping) of the one or more ionic species previously electroplated (e.g., deposited) to the working electrode to be monitored by measuring the electrical current drawn from the working electrode as the electrical potential difference between the working electrode and the reference electrode is altered and varied.

After measuring the electrical current drawn at the working electrode, one or more peaks (e.g., such as a local maximum) within the measured electrical current may be detected, such as by detecting one or more peaks of the electrical current drawn from the working electrode as a function of the measured electrical potential difference between the working electrode and the reference electrode, and/or by detecting one or more peaks from the electrical current drawn from the working electrode as a function of time. For example, these detected peaks of the electrical current drawn from the working electrode may be observed at the measured electrical potential difference, thereby establishing a stripping potential for one or more ionic species when stripped from the working electrode. By observing the detected peaks of the electrical current drawn from the working electrode, one may then determine the concentration of one or more ionic species within the solution (as the same or similar solution was used to deposit one or more ionic species on the working electrode). One or more of these steps of biasing the electrical potential difference, altering the bias of the electrical potential difference, measuring the electrical current drawn from the working electrode, detecting one or more peaks from the drawn current, and/or observing the electrical potential difference at the detected peaks may be repeated and/or re-performed in accordance with the present disclosure. For example, a lower electrical potential difference, as compared to the initial electrical potential difference, may be used when biasing the electrical potential difference between the working electrode and the reference electrode.

Accordingly, a method using anodic stripping voltammetry may be used to determine, such as quantitatively, an amount-of-substance and/or concentration (molality) of one or more ionic species at a solid-liquid interface for a diffusion layer on a working electrode. In one example, anodic stripping voltammetry may be used to detect and determine the molality (concentrations) of ionic species at a range of about one $10^{-6}$ to $10^{-9}$ $g \cdot dm^3$. Anodic stripping voltammetry may also enable one to determine and/or differentiate between one or more ionic species (e.g., nickel ions, chromium ions, molybdenum ions, copper ions, and/or irons ions that is either $Fe^{2+}$, $Fe^{3+}$), such as based upon an ionic species electrical current to electrical potential difference behavior and/or electrical current to time behavior.

To determine a molality of one or more ionic species and/or differentiate between one or more ionic species, a method using anodic stripping voltammetry may include: establishing a correspondence and/or correlation between a stripping potential and an ionic species oxidized (e.g., stripped) at this stripping potential; and may include determining a concentration of the ionic species in the solution from the measured electrical current to electrical potential difference behavior and/or the measured electrical current to time behavior.

In one example, establishing a correspondence and/or correlation between a stripping potential and an ionic species oxidized (e.g., stripped) may be performed by estimating the electrical potential of the reference electrode with respect to a standard hydrogen electrode. The standard hydrogen electrode used may be at a temperature of 298.15 K, have an aqueous molarity of 1 $mol \cdot dm^3$, and may be at standard pressure of 0.1 MPa. For example, a calibration step may be used in the method, in which the electrical potential difference between the working electrode and the reference electrode is increased until the working electrode corrodes. This would enable the electrical potential difference to be measured when the material of the working electrode (such as platinum if used for the working electrode) corrodes to provide a reference point. The values of standard electrode potentials are listed in Table 1 and may be used as a basis to establish a correspondence and/or correlation between a stripping potential and an ionic species oxidized once a reference point is known. However, the measured stripping potentials, when performed downhole with a tool body, may not be at equilibrium, and the measured stripping potentials may be influenced by other media flowing within the fluid. Accordingly, the values listed in Table 1 may only be used as a reference, and may further be refined using experimental data, such as data obtained under downhole conditions.

TABLE 1

The standard electrode potential E° of a half reaction relative to the standard hydrogen electrode at a temperature of 298.15 K, having an aqueous 1 mol · dm³, and at standard pressure of 0.1 MPa.

| Element | Half reaction | E°/V |
|---|---|---|
| Au | $Au^+(aq) + e^- = Au(s)$ | 1.692 |
| Au | $Au^{3+}(aq) + 3e^- = Au(s)$ | 1.498 |
| Pt | $Pt^{2+}(aq) + 2e^- = Pt(s)$ | 1.18 |
| Pd | $Pd^{2+}(aq) + e^- = Pd(s)$ | 0.951 |
| Ag | $Ag^+(aq) + e^- = Ag(s)$ | 0.7996 |
| Cu | $Cu^+(aq) + e^- = Cu(s)$ | 0.521 |
| Cu | $Cu^{2+}(aq) + e^- = Cu(s)$ | 0.3419 |
| $H_2$ | $2H^+(aq) + 2e^- = H_2(g)$ | 0 |
| Fe | $Fe^{3+}(aq) + e^- = Fe(s)$ | -0.037 |
| Pb | $Pb^{2+}(aq) + 2e^- = Pb(s)$ | -0.1262 |
| Sn | $Sn^{2+}(aq) + 2e^- = Sn(s)$ | -0.1375 |
| Ni | $Ni^{2+}(aq) + 2e^- = Ni(s)$ | -0.257 |
| Co | $Co^{2+}(aq) + 2e^- = Co(s)$ | -0.28 |
| Cd | $Cd^{2+}(aq) + 2e^- = Cd(s)$ | -0.403 |
| Fe | $Fe^{2+}(aq) + 2e^- = Fe(s)$ | -0.447 |
| Cr | $Cr^{3+}(aq) + 3e^- = Cr(s)$ | -0.744 |
| Zn | $Zn^{2+}(aq) + 2e^- = Zn(s)$ | -0.7618 |
| Cr | $Cr^{2+}(aq) + 2e^- = Cr(s)$ | -0.913 |
| Mn | $Mn^{2+}(aq) + 2e^- = Mn(s)$ | -1.185 |
| Ti | $Ti^{3+}(aq) + 3e^- = Ti(s)$ | -1.37 |
| Ti | $Ti^{2+}(aq) + 2e^- = Ti(s)$ | -1.63 |
| Al | $Al^{3+}(aq) + 3e^- = Al(s)$ | -1.662 |
| Mg | $Mg^{2+}(aq) + 2e^- = Mg(s)$ | -2.372 |
| Mg | $Mg^+(aq) + e^- = Mg(s)$ | -2.7 |
| Na | $Na^+(aq) + e^- = Na(s)$ | -2.71 |
| Ca | $Ca^{2+}(aq) + 2e^- = Ca(s)$ | -2.868 |
| K | $K^+(aq) + e^- = K(s)$ | -2.931 |
| Li | $Li^+(aq) + e^- = Li(s)$ | -3.041 |
| Ca | $Ca^+(aq) + e^- = Ca(s)$ | -3.8 |

When determining a concentration of the ionic species in the fluid from the measured electrical current to electrical potential difference behavior and/or the measured electrical current to time behavior, one or more steps may be used. In one step, for a given ionic species (such as a $Ni^{2+}$ nickel ion), a concentration of the ionic species in the fluid may be determined from an amplitude of the detected electrical current peak associated with the oxidation (e.g., stripping) of the ionic species from the working electrode. A relationship between the electrical peak current and the concentration of the ionic species may depend on one or more factors, such as a configuration of the electrochemical corrosion transducer having the electrodes within the downhole tool, an amplitude of the bias of the electrical potential difference when depositing the ionic species on the working electrode, a duration of the bias of the electrical potential difference when depositing the ionic species on the working electrode, a rate of altering the bias of the electrical potential difference when stripping the ionic species from the working electrode, and/or the flow of the solution adjacent to the electrochemical corrosion transducer. The relationship between the electrical peak current and the concentration of the ionic species in solution may be determined empirically, such as by performing calibrating the electrochemical corrosion transducer within a controlled environment.

In another step, for a given ionic species, a concentration of the ionic species in the fluid may be determined from an area defined by the measured electrical current curve as a function of the potential difference, such as when measuring the electrical current drawn from the working electrode. For more accurate results, a baseline current may then be used to correct the measured electrical current curve, if desired.

In yet another step, for a given ionic species, a concentration of the ionic species in the fluid may be determined from the stripping voltage of the ionic species with reference to the standard hydrogen electrode at a temperature of 298.15 K, having an aqueous molarity of 1 mol·dm³, and at standard pressure of 0.1 MPa, such as by solving for the molarity c in Equation (1), in which k is Boltzmann's constant, n is the number of electrons exchanged in the oxidation of the given ion (which may be found in Table 1), T the thermodynamic temperature and E° is the standard electrode potential of a half reaction relative to the standard hydrogen electrode at a temperature of 298.15 K, having an aqueous molarity of 1 mol·m³ at standard pressure of 0.1 MPa.

$$E°(T,c)=E°(298\ K,c=1\ mol·dm^3)+(kT/n)\log c \qquad \text{Equation (1)}$$

As such, FIGS. 10A, 10B, and 10C, show multiple schematic views of electrode configurations adapted to voltammetry in accordance with one or more aspects of the present disclosure. In FIG. 10A, a corrosion sensor 1101A may include a reference electrode 1191A and a working electrode 1193A, in which the electrical potential difference and/or the electrical current may be measured between the reference electrode 1191A and the working electrode 1193A. In FIG. 10B, a corrosion sensor 1101B may include a reference electrode 1191B, a working electrode 1193B, and an auxiliary electrode 1195B, in which the auxiliary electrode 1195B may provide stability to the transducer 1101B for the measurement of the electrical potential difference between the reference electrode 1191B and the working electrode 1193B. The electrical current may also be measured in tool 1101B between the working electrode 1193B and the auxiliary electrode 1195B. In FIG. 10C, a tool 1201 may include a reference electrode 1291, multiple working electrodes 1293A to 1293D, and at least one auxiliary electrode 1295. The electrical potential difference may be measured between the reference electrode 1291 and one or more of the working electrodes 1293A to 1293D, in which the working electrodes 1293A to 1293D may each be exposed to a different fluid, or fluid at a different location, that is to be analyzed, and/or the working electrodes 1293A to 1293D may be used to measure multiple ionic species within a fluid. The electrical current may be measured between the working electrodes 1293A to 1293D and the auxiliary electrode 1295, or additional auxiliary electrodes if present. In FIGS. 10A and 10B the flow of solution is indicated by arrows.

Accordingly, using one or more different steps, one may determine a concentration of one or more ionic species in solution and/or differentiate between one or more ionic species using anodic stripping voltammetry with an electrochemical corrosion transducer having two or more electrodes. For example, with reference to FIG. 10B, in which the tool 1101B includes the reference electrode 1191B, the working electrode 1193B, and the auxiliary electrode 1195B, the electrical potential difference between the working electrode 1193B and the reference electrode 1191B may be varied. The electrical potential difference may be varied by biasing the electrical potential difference between the working electrode 1193B and the reference electrode 1191B to deposit one or more ionic species on the working electrode 1193B, and then altering the bias of the electrical potential difference between the working electrode 1193B and the reference electrode 1191B to strip one or more ionic species, at least partially, from the working electrode 1193B. When varying the electrical potential difference between the working electrode 1193B and the reference electrode 1191B, an electrical current may be measured between the working electrode 1193B and the auxiliary electrode 1195B. One or more peaks of the measured electrical current between the working electrode 1193B and the auxiliary electrode 1195B may be detected, in which the electrical potential difference between the working electrode 1193B and the reference electrode 1191B may be observed at the detected peaks of the measured electrical current. Then, using one or more of the steps discussed above, a concentration of one or more ionic species within the fluid exposed to the tool 1101B may be determined based upon the observed electrical potential difference at the detected peaks of the measured electrical current.

Figure 11:
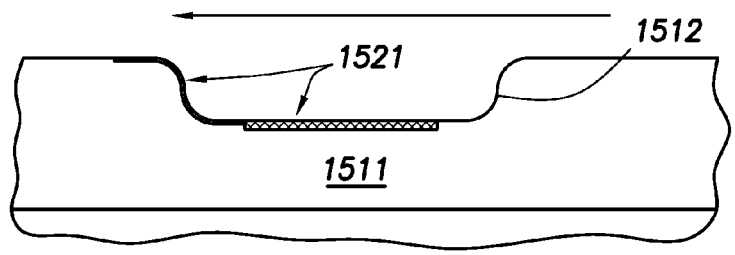
FIG. 11 is a schematic view of apparatus according to one or more aspects of the present disclosure.

Referring now to FIG. 11, illustrated is a schematic view of a downhole tool 1511 in accordance with one or more aspects of the present disclosure. As shown, the downhole tool 1511 may include a perturbation 1512, such as a perturbation 1512 formed thereon or included therewith. The perturbation 1512 may be used generate turbulence within the fluid (or solution) flowing adjacent to a corrosion sensor 1521. This may enable the corrosion sensor 1521 to be exposed to a more representative sample of the solution adjacent to the downhole tool 1511. The perturbation 1512, as shown, may be a depression formed within the downhole tool 1511. The perturbation 1512 may also include a recess or upset formed on the downhole tool 1511, and/or may include a groove formed on the downhole tool 1511. However, those having ordinary skill in the art will appreciate that one or more other perturbations may be used with a downhole tool without departing from the scope of the present disclosure.

Figure 12A:
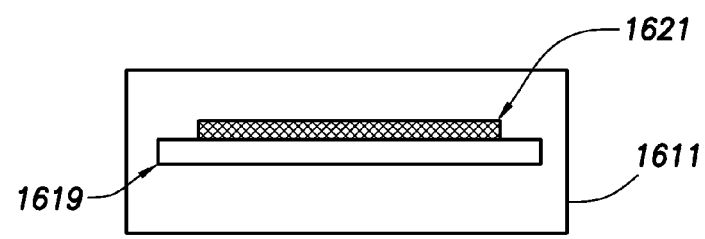
FIGS. 12A and 12B are schematic views of apparatus according to one or more aspects of the present disclosure.
Figure 12B:
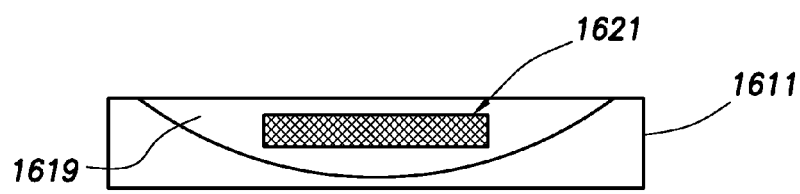

Alternative arrangements in accordance with the present disclosure for a downhole tool having a corrosion sensor coupled thereto are also contemplated. For example, FIG. 12A shows a top schematic view and FIG. 12B shows a sectional schematic view of a downhole tool 1611 having a corrosion sensor 1621 coupled thereto. The downhole tool 1611 may have a passage 1619 formed there through, in which the corrosion sensor 1621 may be disposed on one side of the passage 1619 to measure an effect of corrosion within the passage 1619. The passage 1619 may also be selectively sized, for example, to prevent particulate and/or debris from entering into the passage 1619, if desired.

Figure 13A:
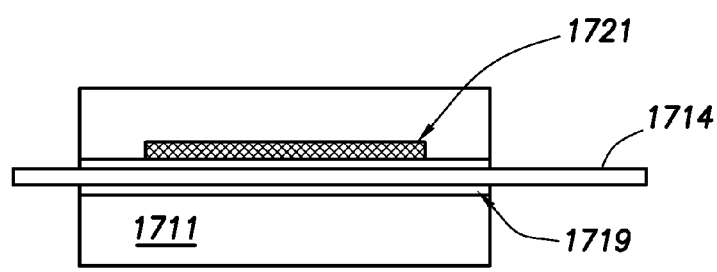
FIGS. 13A and 13B are schematic views of apparatus according to one or more aspects of the present disclosure.
Figure 13B:
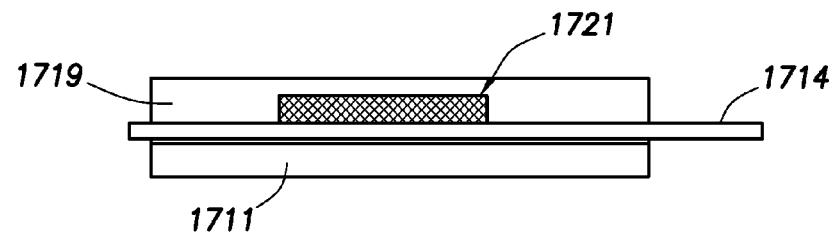

In another example, FIG. 13A shows a top schematic view and FIG. 13B shows a sectional schematic view of a downhole tool 1711 having a corrosion sensor 1721 coupled thereto. The downhole tool 1711 may have a groove 1719 formed there through, in which the corrosion sensor 1721 may be disposed adjacent to the groove 1719. The downhole tool 1711, which may be a wireline tool, may include a wireline 1714 attached thereto. As such, the corrosion sensor 1721 may be used to measure one or more properties of the fluid within the groove 1719 with respect to the downhole tool 1711 and/or the wireline 1714.

Accordingly, a corrosion sensor in accordance with the present disclosure may be used to measure an effect of corrosion of the metal material exposed to a fluid, such as a downhole fluid. The metal material may be in direct contact with the fluid, such as having a face of the sensor directly exposed to fluid flowing across the sensor, or may be in indirect contact with the fluid, such as by having a material layer disposed over the corrosion sensor. This metal material may then be a part of a tool, such as a part of the tool body.

The present disclosure may provide for one or more of the following advantages. A tool and method in accordance with the present disclosure may be included within one or more of the tools and/or devices that may be disposed downhole within a subterranean formation. A tool and a method in accordance with the present disclosure may be able to measure one or more properties of a fluid from which a tool may be exposed to downhole, such as measure one or more corrosive properties of the fluid and/or measure one or more properties of the fluid indicating corrosion of a tool. Based upon the measured effect of corrosion, this may enable the composition of the fluid measured downhole within the borehole to be modified, such as by adding one or more components to the fluid, to thereby adjust the measured corrosion effect.

In view of all of the above and the figures, those skilled in the art should readily recognize that the present disclosure introduces an apparatus comprising: at least a portion of a metal material configured to be disposed within a borehole, the borehole extending into a subterranean formation, the at least portion of the metal material configured to be exposed to a fluid; and a sensor configured to measure an effect of corrosion of the at least portion of the metal material within the fluid. At least portion of the metal material may be in direct contact with the fluid. The at least portion of the metal material may be part of a tool body, wherein the sensor may be coupled to the tool body, and wherein the tool body may be configured to be exposed, at least partially, to the fluid. The sensor may comprise an electrochemical corrosion transducer. The electrochemical corrosion transducer may comprise a working electrode and a reference electrode. The sensor may be configured to measure an electrical potential difference between the working electrode and the reference electrode. The sensor may be configured to measure an electrical current between the working electrode and the reference electrode. The sensor may be configured to vary an electrical potential difference between the working electrode and the reference electrode. The electrochemical corrosion transducer may further comprise an auxiliary electrode, and wherein the sensor may be configured to measure an electrical current between the working electrode and the auxiliary electrode. At least one of the working electrode and the reference electrode may comprise an inert material, wherein the inert material may comprise platinum. The working electrode may comprise an electrical contact electrically coupled to the tool body, and wherein the reference electrode may be part of an electrochemical cell electrically coupled to the electrical contact. The electrochemical corrosion transducer may comprise: an electrical contact electrically coupled to the tool body; an electronics unit electrically coupled to the electrical contact; and an electrochemical cell electrically coupled to the electronics unit; wherein the electronics unit is configured to measure an electrical potential difference between the electrical contact and the electrochemical cell. The electronics unit may comprise: an operational amplifier having an inverting input, a non-inverting input, and an output, wherein the electrochemical cell is electrically coupled to the non-inverting input of the operational amplifier; a capacitor electrically coupled between the electrical contact and the inverting input of the operational amplifier; a resistor electrically coupled between the output of the operational amplifier and the inverting input of the operational amplifier; and a voltmeter electrically coupled across the capacitor. The electrochemical cell may comprise a housing having the reference electrode disposed within a fluid therein. The reference electrode may comprise a material similar to that of the at least portion of the metal material, and wherein a fluid of the electrochemical cell may comprise a preselected fluid. The electrochemical corrosion transducer may be thermally coupled to the tool body using a heat sink The fluid may be flowing across the electrochemical transducer such that the fluid is exposed to the working electrode before the reference electrode. The fluid may be flowing downhole within the borehole in a passage formed within the tool body. The fluid may be flowing uphole within the borehole in an annulus formed between the tool body and the borehole. The tool body may comprise at least one of an upset and a recess formed thereon, and wherein the sensor may be disposed adjacent to the at least one of the upset and the recess. The tool body may comprise a groove formed thereon, wherein the sensor is disposed, at least partially, within the groove. A wireline cable may be disposed adjacent to the groove of the tool body. The apparatus may further comprise: at least a portion of a second metal material configured to be disposed within the borehole and configured to be exposed to a fluid; and a second sensor configured to measure an effect of corrosion of the at least portion of the second metal material within the fluid. At least one of the at least portion of the first metal material and the at least portion of the second metal material may be part of a tool body. The first sensor may be disposed at a first location on the tool body and the second sensor may be disposed at a second location on the tool body. The first sensor may be configured to measure the effect of corrosion within a passage formed within the tool body, and wherein the second sensor may be configured to measure the effect of corrosion within an annulus formed between the tool body and the borehole. The at least portion of the first metal material and the at least portion of the second metal material may comprise different metal materials. The fluid may comprise at least one of a drilling fluid, a completion fluid, an injection fluid, and a subterranean formation fluid. The apparatus may further comprise a telemetry unit coupled to the sensor and configured to transmit the measured effect of corrosion to a surface unit. The sensor may be configured to measure a concentration of at least one ionic species within the fluid exposed to the at least portion of the metal material. The sensor may be configured to compare an electrical potential of the at least portion of the metal material with an electrical potential of a second metal material exposed to a predetermined fluid. The sensor may be configured to measure an electrical potential difference between the at least portion of the metal material and a second metal material exposed to a predetermined fluid. The at least portion of the metal material may be part of a wireline cable. The at least portion of the metal material may be part of a wired drill pipe, wherein the sensor may comprise a plurality of sensors configured to measure an effect of corrosion of the at least portion of the metal material within the fluid, wherein the plurality of sensors may be distributed along a length of the wired drill pipe. The sensor may be disposed within a cavity of a tool body, wherein the cavity may comprise a piston disposed therein configured to pump the fluid within the cavity.

The present disclosure also introduces a method comprising: disposing at least a portion of a metal material within a borehole, the borehole extending into a subterranean formation; and measuring an effect of corrosion of the at least portion of the metal material within a fluid exposed to the at least portion of the metal material with a sensor. The method may further comprise directly contacting the fluid with the at least portion of the metal material. The at least portion of the metal material may be part of a tool body, wherein the sensor may be coupled to the tool body, and wherein the tool body may be exposed, at least partially, to the fluid. The sensor may comprise an electrochemical corrosion transducer. The electrochemical corrosion transducer may comprise a working electrode and a reference electrode, wherein the measuring the effect of corrosion may comprise at least one of: measuring an electrical potential difference between the working electrode and the reference electrode; and measuring an electrical current between the working electrode and the reference electrode. The method may further comprise varying the electrical potential difference between the working electrode and the reference electrode. The electrochemical corrosion transducer may comprise an electrical contact, an electrochemical cell, and an electronics unit, wherein the measuring the effect of corrosion comprises measuring an electrical potential difference between the electrical contact and the electrochemical cell with the electronics unit. A working electrode may comprise the electrical contact, wherein the electrical contact may be electrically coupled to the tool body, wherein a reference electrode may be part of the electrochemical cell, and wherein the electrochemical cell may be electrically coupled to the electrical contact. The electrochemical corrosion transducer may comprise a working electrode, a reference electrode, and an auxiliary electrode, wherein the measuring the effect of corrosion may comprise: varying an electrical potential difference between the working electrode and the reference electrode; and measuring an electrical current between the working electrode and the auxiliary electrode. The varying the electrical potential difference may comprise: biasing the electrical potential difference between the working electrode and the reference electrode; and altering the bias of the electrical potential difference between the working electrode and the reference electrode. The biasing the electrical potential difference may comprise depositing at least one ionic species on the working electrode, and wherein the altering the bias of the electrical potential difference may comprise stripping the at least one ionic species, at least partially, from the working electrode. The measuring the effect of corrosion may further comprise: detecting at least one peak of the measured electrical current between the working electrode and the auxiliary electrode; and observing the electrical potential difference between the working electrode and the reference electrode at the detected at least one peak of the measured electrical current. The measuring the effect of corrosion may further comprise determining a concentration of at least one ionic species within the fluid based upon the observed electrical potential difference at the detected at least one peak of the measured electrical current. The method may further comprise comparing the measured effect of corrosion with a predetermined range. If the measured effect of corrosion is not within the predetermined range, the method further comprises at least one of: modifying a composition of the fluid, thereby adjusting the measured effect of corrosion; and removing the tool body from the borehole, thereby removing the at least portion of the metal material from the borehole. The fluid may be flowing across the electrochemical transducer such that the fluid is exposed to a working electrode before a reference electrode. The fluid may be flowing downhole within the borehole in a passage formed within the tool body. The fluid may be flowing uphole within the borehole in an annulus formed between the tool body and the borehole. The tool body may comprise at least one of an upset and a recess formed thereon, and wherein the sensor may be disposed adjacent to at least one of the upset and the recess. The method may further comprise transmitting the measured effect of corrosion to a surface unit with a telemetry unit coupled to the sensor. The fluid may comprise at least one of a drilling fluid, a completion fluid, an injection fluid, and a subterranean formation fluid. The method may further comprise: disposing at least a portion of a second metal material within the borehole; and measuring an effect of corrosion of the at least portion of the second metal material within a second fluid exposed to the at least portion of the second metal material with a second sensor. At least one of the at least portion of the first metal material and the at least portion of the second metal material may be part of a tool body. The first sensor may be configured to measure the effect of corrosion within a passage formed within the tool body, and wherein the second sensor may be configured to measure the effect of corrosion within an annulus formed between the tool body and the borehole. The at least portion of the first metal material and the at least portion of the second metal material may comprise different metal materials. The first sensor may be disposed at a first location within the borehole, and wherein the second sensor may be disposed at a second location within the borehole, the method may further comprise: comparing the measurement of the effect of corrosion of the at least portion of the first metal material with the measurement of the effect of corrosion of the at least portion of the second metal material; and determining an influx of fluid from the subterranean formation into the borehole based upon the comparison of the measurements of the effect of corrosion. The method may further comprise: monitoring an influx of gas from the subterranean formation into the borehole based upon the measurement of the effect of corrosion of the at least portion of the first metal material and the measurement of the effect of corrosion of the at least portion of the second metal material. The method may further comprise: measuring a strength of corrosivity of a fluid pumped from the borehole with a second corrosion sensor. The method may further comprise at least one of: removing the at least portion of the metal material from the borehole based upon the measurement of the effect of corrosion of the at least portion of the first metal material; disposing at least a portion of a second metal material within the borehole, the at least portion of the second metal material selected based upon the measurement of the effect of corrosion of the at least portion of the first metal material; and completing a well having the borehole, at least partially, with a metal alloy selected based upon the measurement of the effect of corrosion of the at least portion of the first metal material.

The present disclosure also introduces an apparatus comprising: a downhole tool configured for conveyance within a borehole extending into a subterranean formation; at least a portion of a metal material coupled with the downhole tool and configured to be exposed to a fluid; and a sensor coupled with the downhole tool and configured to measure an effect of corrosion of the at least portion of the metal material within the fluid, wherein the sensor comprises an electrochemical corrosion transducer. The at least portion of the metal material may be part of a tool body of the downhole tool, wherein the sensor is coupled to the tool body, and wherein the tool body is configured to be at least partially exposed to the fluid.

The electrochemical corrosion transducer may comprise a working electrode and a reference electrode, and the sensor may be configured to: measure an electrical current between the working electrode and the reference electrode; measure an electrical potential difference between the working electrode and the reference electrode; and/or vary an electrical potential difference between the working electrode and the reference electrode.

The electrochemical corrosion transducer may comprise a working electrode, a reference electrode and an auxiliary electrode, and the sensor may be configured to measure an electrical current between the working electrode and the auxiliary electrode.

The electrochemical corrosion transducer may comprise a working electrode and a reference electrode, and the working electrode may comprise an electrical contact electrically coupled to the tool body, and wherein the reference electrode is part of an electrochemical cell electrically coupled to the electrical contact.

The electrochemical corrosion transducer may comprise: an electrical contact electrically coupled to the tool body; an electronics unit electrically coupled to the electrical contact; and an electrochemical cell electrically coupled to the electronics unit; wherein the electronics unit is configured to measure an electrical potential difference between the electrical contact and the electrochemical cell. The electrochemical corrosion transducer may comprise a working electrode and a reference electrode, and the electrochemical cell may comprise a housing having the reference electrode disposed within an additional fluid therein. The reference electrode may comprise a material similar to that of the at least portion of the metal material.

The metal material may be a first metal material, the sensor may be a first sensor, and the apparatus may further comprise: at least a portion of a second metal material coupled with the downhole tool and configured to be exposed to the fluid; and a second sensor coupled with the downhole tool and configured to measure an effect of corrosion of the at least portion of the second metal material within the fluid, and the first and second sensors may be disposed at different locations of the downhole tool. At least one of the at least portion of the first metal material and the at least portion of the second metal material may be part of a tool body of the downhole tool.

The fluid may comprise at least one of a drilling fluid, a completion fluid, an injection fluid, and a subterranean formation fluid.

The apparatus may further comprise a telemetry unit coupled to the sensor and configured to transmit the measured effect of corrosion to a surface unit.

The sensor may be configured to measure a concentration of at least one ionic species within the fluid exposed to the at least portion of the metal material.

The fluid may be a first fluid and the sensor may be configured to compare an electrical potential of the at least portion of the metal material with an electrical potential of an additional metal material exposed to a second fluid.

The fluid may be a first fluid, and the sensor may be configured to measure an electrical potential difference between the at least portion of the metal material and an additional metal material exposed to a second fluid.

The at least portion of the metal material may be part of a wireline cable.

The at least portion of the metal material may be part of a wired drill pipe, the sensor may comprise a plurality of sensors configured to measure an effect of corrosion of the at least portion of the metal material within the fluid, and the plurality of sensors may be distributed along a length of the wired drill pipe.

The sensor may be disposed within a cavity of a tool body of the downhole tool, and the cavity may comprise a piston disposed therein configured to pump the fluid within the cavity.

The foregoing outlines feature several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A system, comprising:
a downhole tool configured for conveyance within a borehole extending into a subterranean formation and comprising a metal portion exposed to a flow path for a downhole fluid; and
an electrochemical corrosion sensor comprising:
an electrical contact coupled to the metal portion;
an electrochemical cell housing a reference fluid substantially similar to the downhole fluid;
a reference electrode disposed in the reference fluid; and
an electronics unit coupled to the electrical contact and the reference electrode to monitor, based on a measured electrical potential difference, corrosiveness of the downhole fluid.

2. The system of claim 1 wherein the reference electrode comprises a material similar to that of metal portion.

3. The system of claim 1 wherein the downhole fluid comprises at least one of a drilling fluid, a completion fluid, an injection fluid, and a subterranean formation fluid.

4. The system of claim 1 wherein the metal portion is part of a wireline cable.

5. The system of claim 1 wherein the metal portion is part of a wired drill pipe.

6. The system of claim 1 wherein the sensor is disposed within a cavity of a tool body of the downhole tool, wherein the cavity comprises a piston disposed therein and configured to pump the fluid within the cavity.

7. The system of claim 1 comprising a telemetry unit coupled to the sensor to transmit an indicator of the corrosiveness to a surface unit.

8. The system of claim 1 comprising a control system configured to receive an indication of the corrosiveness from the sensor and to generate an alert in response to determining that the corrosiveness is outside a desired range.

9. The system of claim 1 comprising a control system configured to analyze the corrosiveness and recommend a change in composition of the downhole fluid based on the analysis.

10. The system of claim 1, wherein the metal portion comprises a flow line configured to direct formation fluid into the downhole tool from the subterranean formation.

11. A system comprising:
a downhole tool configured for conveyance within a borehole extending into a subterranean formation and comprising a metal body defining an internal flow path through the downhole tool for a drilling fluid; and
a first electrochemical corrosion sensor comprising:
an electrical contact coupled to the metal body;
an electrochemical cell housing a reference fluid substantially similar to a downhole fluid;
a reference electrode disposed in the reference fluid; and
an electronics unit coupled to the electrical contact and the reference electrode to monitor, based on a measured electrical potential difference, a first corrosiveness of the drilling fluid flowing through the internal flow path.

12. The system of claim 11 comprising a second electrochemical corrosion sensor coupled to an outer body of the downhole tool to monitor a second corrosiveness of the drilling fluid flowing past the outer body of the downhole tool.

13. The system of claim 12 comprising a control system configured to compare the first corrosiveness to the second corrosiveness to determine whether a formation fluid is entering the borehole from the subterranean formation.

14. The system of claim 12, wherein the metal body comprises a chassis and wherein the outer body comprises a drill collar.

15. The system of 11, wherein the first electrochemical corrosion sensor comprises a heat sink coupled to the metal body and the electrochemical cell.

16. The system of claim 11, comprising a control system configured to receive an indication of the corrosiveness from the first electrochemical corrosion sensor and to generate an alert in response to determining that the corrosiveness is outside a desired range.

* * * * *